(12) United States Patent
Weimer et al.

(10) Patent No.: US 7,220,596 B2
(45) Date of Patent: May 22, 2007

(54) REAL TIME DETECTION OF ANTIGENS

(75) Inventors: Bart C. Weimer, Logan, UT (US); Marie K. Walsh, North Logan, UT (US)

(73) Assignee: Utah State University, Logan, UT (US)

( * ) Notice: Subject to any disclaimer, the term of this patent is extended or adjusted under 35 U.S.C. 154(b) by 578 days.

(21) Appl. No.: 10/317,853

(22) Filed: Dec. 11, 2002

(65) Prior Publication Data

US 2004/0009529 A1   Jan. 15, 2004

Related U.S. Application Data

(63) Continuation-in-part of application No. 10/163,253, filed on Jun. 4, 2002, now abandoned, which is a continuation-in-part of application No. 09/292,172, filed on Apr. 15, 1999, now Pat. No. 6,399,317.

(60) Provisional application No. 60/081,889, filed on Apr. 15, 1998.

(51) Int. Cl.
*G01N 33/543* (2006.01)

(52) U.S. Cl. ...................... 436/518; 435/7.1; 435/7.92; 435/286.5; 436/524; 210/656; 210/661

(58) Field of Classification Search ................ 435/7.1, 435/7.92–7.94, 286.5, 288.6, 962; 436/518, 436/523–527, 174, 175; 210/616, 617, 656, 210/661
See application file for complete search history.

(56) References Cited

U.S. PATENT DOCUMENTS

| | | | |
|---|---|---|---|
| 1,716,321 A | 6/1929 | Pearson | |
| 2,798,718 A | 7/1957 | Gross | |
| 3,002,092 A | 9/1961 | Cary | |
| 3,025,142 A | 3/1962 | Williams | |
| 3,492,396 A | 1/1970 | Dalton et al. | |
| 3,600,063 A | 8/1971 | Bowen | |
| 3,740,552 A | 6/1973 | Pressman | |
| 3,947,352 A | 3/1976 | Cuatrecasas et al. | |
| 4,059,685 A | 11/1977 | Johnson | |
| 4,153,675 A | 5/1979 | Kleinerman | |
| 4,157,323 A | 6/1979 | Yen et al. | |
| 4,173,392 A | 11/1979 | Ekinaka et al. | |
| 4,201,831 A | 5/1980 | Slusarczuk et al. | |
| 4,217,338 A | 8/1980 | Quash | |
| 4,225,487 A | 9/1980 | Cuatrecasas et al. | |
| 4,268,171 A | 5/1981 | Sternberg | |
| 4,314,905 A | 2/1982 | Etzel et al. | |
| 4,347,244 A | 8/1982 | Mynard et al. | |
| 4,348,107 A | 9/1982 | Leif | |
| 4,352,884 A | 10/1982 | Nakashima et al. | |
| 4,425,438 A | 1/1984 | Bauman et al. | |
| 4,454,234 A | 6/1984 | Czerlinski | |
| 4,469,787 A | 9/1984 | Woods et al. | |
| 4,478,946 A | 10/1984 | Van der Merwe et al. | |
| 4,483,807 A | 11/1984 | Asano et al. | |
| 4,495,074 A | 1/1985 | Hagiwara et al. | |
| 4,505,260 A | 3/1985 | Metzger | |
| 4,582,809 A | 4/1986 | Block et al. | |
| 4,585,623 A | 4/1986 | Chandler | |
| 4,652,518 A | 3/1987 | Makela et al. | |
| 4,652,533 A | 3/1987 | Jolley | |
| 4,668,591 A | 5/1987 | Minemura et al. | |
| 4,678,268 A | 7/1987 | Russo et al. | |
| 4,713,347 A | 12/1987 | Mitchell et al. | |
| 4,714,345 A | 12/1987 | Schrader | |
| 4,732,811 A | 3/1988 | Margel | |
| 4,738,773 A | 4/1988 | Müller-Ruchholtz et al. | |
| 4,775,515 A | 10/1988 | Cottingham | |
| 4,780,423 A | 10/1988 | Bluestein et al. | |
| 4,837,305 A | 6/1989 | Goodman et al. | |
| 4,895,650 A | 1/1990 | Wang | |
| 4,912,051 A | 3/1990 | Zaromb | |
| 4,963,498 A | 10/1990 | Hillman et al. | |

(Continued)

FOREIGN PATENT DOCUMENTS

| CA | 1 152 898 | 8/1983 |
|---|---|---|
| EP | 0 206 077 | 12/1986 |
| EP | 0 317 286 | 5/1989 |
| EP | 0 382 215 | 8/1990 |
| EP | 0 404 258 | 12/1990 |
| EP | 0 170 697 | 10/1991 |
| GB | 1 439 175 | 6/1976 |
| SU | 1507-421 A | 5/1987 |
| SU | 1572-678 A | 5/1988 |
| WO | 81/02529 | 9/1981 |
| WO | 87/01608 | 3/1987 |
| WO | 87/05003 | 8/1987 |
| WO | 90/07380 | 7/1990 |

OTHER PUBLICATIONS

Manca et al., Antigenicity of HIV-derived T Helper determinants in the context of carrier recombinant proteins: Effect on T helper cell repertoire selection. European Journal of Immunology, (1996) vol. 26, No. 10, abstract only.*

(Continued)

*Primary Examiner*—Long V. Le
*Assistant Examiner*—Gary W. Counts
(74) *Attorney, Agent, or Firm*—Clayton, Howarth & Cannon, P.C.

(57) ABSTRACT

Antigens can be captured and detected from complex samples, such as food and environmental samples, in about 30 minutes using apparatus and methods that include flow of the samples through a module containing antibodies coupled to beads. The samples flow through the modified beads at about 0.2 to 1.2 liters/minute, which fluidizes the bead bed. The antigens are captured by the antibodies, and then detection of the captured antibodies is carried out with chemiluminescence, fluorescence, or spectrophotometric techniques.

26 Claims, 15 Drawing Sheets

U.S. PATENT DOCUMENTS

| | | | |
|---|---|---|---|
| 5,110,624 A | | 5/1992 | Noble et al. |
| 5,110,727 A | | 5/1992 | Oberhardt |
| 5,120,643 A | | 6/1992 | Ching et al. |
| 5,147,777 A | | 9/1992 | Sutton et al. |
| 5,183,486 A | | 2/1993 | Gatten et al. |
| 5,183,740 A | | 2/1993 | Ligler et al. |
| 5,192,551 A | | 3/1993 | Willoughby, Jr. et al. |
| 5,216,130 A | * | 6/1993 | Line et al. ............ 530/362 |
| 5,225,330 A | | 7/1993 | Ginsburg et al. |
| 5,235,028 A | * | 8/1993 | Barany et al. ............ 528/335 |
| 5,240,602 A | | 8/1993 | Hammen |
| 5,240,640 A | | 8/1993 | Siiman et al. |
| 5,292,840 A | | 3/1994 | Heilmann et al. |
| 5,314,830 A | | 5/1994 | Anderson et al. |
| 5,372,783 A | | 12/1994 | Lackie |
| 5,395,754 A | * | 3/1995 | Lambotte et al. ............ 435/7.4 |
| 5,437,983 A | | 8/1995 | Watts et al. |
| 5,466,609 A | | 11/1995 | Siiman et al. |
| 5,501,863 A | | 3/1996 | Rössling et al. |
| 5,512,659 A | | 4/1996 | Ullman et al. |
| 5,552,086 A | | 9/1996 | Siiman et al. |
| 5,554,340 A | | 9/1996 | Lackie |
| 5,565,365 A | | 10/1996 | Glass |
| 5,620,858 A | | 4/1997 | Armstrong et al. |
| 5,627,233 A | | 5/1997 | Hubbell et al. |
| 5,637,576 A | | 6/1997 | Heerze et al. |
| 5,639,620 A | | 6/1997 | Siiman et al. |
| 5,665,561 A | | 9/1997 | Tuomanen et al. |
| 5,665,582 A | | 9/1997 | Kausch et al. |
| 5,707,877 A | | 1/1998 | Siiman et al. |
| 5,713,943 A | | 2/1998 | Lindegren |
| 5,721,109 A | | 2/1998 | Yano et al. |
| 5,776,706 A | | 7/1998 | Siiman et al. |
| 5,843,633 A | | 12/1998 | Yin et al. |
| 5,858,534 A | | 1/1999 | Sucholeiki |
| 5,858,802 A | | 1/1999 | Chai-Gao et al. |
| 5,928,880 A | * | 7/1999 | Wilding et al. ............ 435/7.21 |
| 6,120,734 A | | 9/2000 | Lackie |
| 6,193,953 B1 | | 2/2001 | Lohrmann et al. |
| 6,277,257 B1 | * | 8/2001 | Paul et al. ............ 204/450 |

OTHER PUBLICATIONS

Blake et al., Imunomagnetic Detection of *Bacillus stearothermophilus* Spores in Food and Environmental Samples, Applied and Environmental Microbiology, May 1997, p. 1643-1646.*

Forrest, "Development and Application of a Fully Automated Continuous Flow Radioimmunoassay System," Ann. clin. Biochem., 14, 1-11, 1977.

Freytag et al., "A Highly Sensitive Affinity-Column-Mediated Immunometric Assay, as Exemplified by Digoxin," Clin. Chem., $3/3$, 417-420, 1984.

Freytag et al., "Affinity-Column-Mediated Immunoenzymometric Assays: Influence of Affinity-Column Ligand and Valency of Antibody-Enzyme Conjugates," Clin. Chem., $3/3$, 1494-1498, 1984.

Friguet et al., "Measurements of the True Affinity Constant in Solution of Antigen-Antibody Complexes by Enzyme-Linked Immunosorbent Assay," Journal of Immunological Methods, 77, 305-319, 1985.

Glaser, "Antigen-Antibody Binding and Mass Transport by Convection and Diffusion to a Surface: A Two-Dimensional Computer Model of Binding and Dissociation Kinetics," Analytical Biochemistry, 213, 152-161, 1993.

Gübitz et al., "Flow-injection immunoassays," Analytica Chimica Acta, 283, 421-428, 1993.

Gunaratna et al., Noncompetitive Flow Injection Immunoassay for Hapten, α-(Difluoromethyl)ornithine, Anal. Chem., 65, 1152-1157, 1993.

Hudson, Jr., *Infrared System Engineering*, Wiley-Interscience, 289 and 294-296, 1969.

Jolley et al., "Particle Concentration Fluorescence Immunoassay (PCFIA): a New, Rapid Immunoassay Technique with High Sensitivity," Journal of Immunological Methods, 67, 21-35, 1984.

O'Shannessy, et al., "Determination of Rate and Equilibrium Binding Constants for Macromolecular Interactions Using Surface Plasmon Resonance: Use of Nonlinear Least Squares Analysis Methods," Anal. Biochem., 212, 457-468, 1993.

Ordentlich et al., "Rhizosphere Colonization by *Serratia Marcescens* for the Control of *Sclerotium Rolfsil*," Soil. Biol. Biochem., 19, 747-751, 1987.

Plant et al., "Lipsome-Enhanced Flow Injection Immunoanalysis," Biotechnology, 6, 266-269, 1988.

Pollema et al., "Sequential Injection Immunoassay Utilizing Immunomagnetic Beads," Analytical Chemistry, 64, 1356-1361, 1992.

Pollema et al., "Flow Injection Renewable Surface Immunoassay: A New Approach to Immunoanalysis with Fluorescence Detection," Anal. Chem., 66, 1825-1831, 1994.

Sambucetti et al., "Process for Purification of Magnetic Ink," IBM Technical Disclosure Bulletin, 18, 593-595, 1975.

Sato et al., "A Novel Method for Isolating Specific Endocytic Vesicles Using Very Fine Ferrite Particles Coated with Biological Ligands and the High-Gradient Magnetic Separation Technique," J. Biochem., 100, 1481-1492, 1986.

Smith, Modern Optical Engineering: The Design of Optical Systems, McGraw-Hill, Inc. (pubs), 1966.

Blake, M.R. et al., "Immunomagnetic Detection of *Bacillus stearothermophilus* Spores in Food and Environmental Samples," Applied and Environmental Microbiology, 63 (5), pp. 1643-1646, May 1997.

"Food Safety: Magnetic Beads Detect Spores," Food Ingredient News, 5 (6), Jun. 1997.

Manca, F. et al., "Antigenicity of HIV-derived T helper determinants in the context of carrier recombinant proteins: effect on T helper cell repertoire selection," European Journal of Immunology, 26 (10), pp. 2461-2469 (abstract only), OCt. 1996.

* cited by examiner

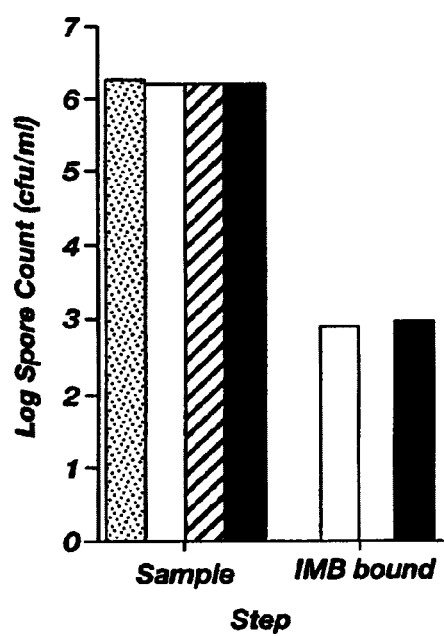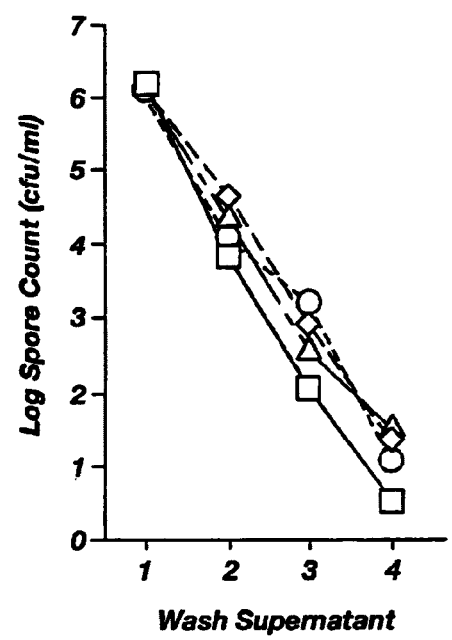
Fig. 1A                    Fig. 1B

REAL TIME DETECTION OF ANTIGENS

CROSS-REFERENCE TO RELATED APPLICATIONS

This application is a continuation-in-part of U.S. Ser. No. 10/163,253, filed Jun. 4, 2002, abandoned, which is a continuation-in-part of U.S. Ser. No. 09/292,172, filed Apr. 15, 1999, now U.S. Pat. No. 6,399,317, which claims the benefit of U.S. Provisional Application No. 60/081,889, filed Apr. 15, 1998, all of which are hereby incorporated by reference in their entireties.

STATEMENT REGARDING FEDERALLY SPONSORED RESEARCH OR DEVELOPMENT

Not applicable.

BACKGROUND OF THE INVENTION

This invention relates to detection of antigens. More particularly, the invention relates to compositions and methods for detection of selected antigens in real time. In an illustrative embodiment, the invention relates to compositions and processes for sensitive detection of microbes and contaminants in complex samples, such as food samples, environmental samples, and the like, within about 30 minutes.

Bacterial spores are the most heat-stable form of microorganisms, are ubiquitous in the environment, and are therefore of great concern in food products, such as milk, that receive extensive heat treatments to prolong shelf life. Spore counts in milk from around the world vary from zero to greater than 22,000 cfu/ml depending on the climate of the region. S. A. Chen et al., A Rapid, Sensitive and Automated Method for Detection of *Salmonella* Species in Foods using AG-9600 AmpliSensor Analyzer, 83 J. Appl. Microbiol. 314-321 (1997). *Bacillus stearothermophilus* spores are one of the most heat-resistant bacterial spores and are found in high numbers in soil and water. Contaminating *B. stearothermophilus* spores survive extreme heat to germinate and grow at elevated product storage temperatures, which occur in foods transported in equatorial regions of the world.

While *B. stearothermophilus* is not commonly a problem, other bacilli often lead to food-borne illness or spoilage in a variety of foods. *Bacillus cereus, Bacillus licheniformis, Bacillus subtilis*, and *Bacillus pumilus* have all been implicated in outbreaks of food-borne illness and are commonly isolated from raw and heat treated milk. M.W. Griffiths, Foodborne Illness Caused by *Bacillus* spp. other than *B. cereus* and Their Importance to the Dairy Industry, 302 Int. Dairy Fed. Bulletin 3-6 (1995). *B. cereus* is also responsible for a sweet curdling defect in milk as well as being pathogenic. W.W. Overcast &K. Atmaram, The Role of *Bacillus cereus* in Sweet Curdling of Fluid Milk, 37 J. Milk Food Technol. 233-236 (1973). A mesophilic heat resistant *bacillus* similar to *Bacillus badius*, has been isolated from extreme temperature processed milk ($D_{147}$=5 sec; P. Hammer et al., Pathogenicity Testing of Unknown Mesophilic Heat Resistant Bacilli from UHT-milk, 302 Int. Dairy Fed. Bulletin 56-57 (1995)). *B. badius* is a mesophilic organism and grows readily at room temperature, making it a likely candidate for spoiling temperature-processed foods. There have been 52 confirmed cases of *B. badius* in UHT milk in Europe and two cases outside of Europe. P. Hammer et al., supra. Lack of a rapid spore assay that can be used in milk contributes to the difficulty of prediction of post processing spoilage, thereby limiting the shelf life and product safety. H. Hofstra et al., Microbes in Food-processing Technology, 15 FEMS Microbiol. Rev. 175-183 (1994). Such an assay could be used in a hazard analysis critical control point (HACCP) plan allowing raw materials with high spore loads to be diverted to products that do not pose a food safety risk to consumers.

The standard method for quantifying spores in milk involves heat-shocking and an overnight plate count. G. H. Richardson, Standard Methods for the Examination of Dairy Products (1985). This is time-consuming and yields historical information. The food industry needs microbiological assays to yield predictive information for maximum benefit in HACCP analysis and risk assessment. An enzyme-linked immunosorbent assay (ELISA) capable of detecting greater than $10^6$ cfu/ml of *B. cereus* spores in foods has been reported, but was unacceptable due to antibody cross-reactivity. Y. H. Chang & P. M. Foegeding, Biotin-avidin Enzyme-linked Immunosorbent Assay for *Bacillus* Spores in Buffer and Food, 2 J. Rapid Methods and Autom. Microbiol. 219-227 (1993).

Techniques to increase sensitivity of immunosorbent assays have focused on more efficient reporter labels, such as faster catalyzing reporter-enzymes; signal amplification, such as avidin- or streptavidin-biotin enzyme complexes; and better detectors, such as luminescence and fluorescence. L. J. Kricka, Selected Strategies for Improving Sensitivity and Reliability of Immunoassays, 40 Clin. Chem. 347-357 (1994); P. Patel, Rapid Analysis Techniques in Food Microbiology (1994). Immunomagnetic antigen capture is used extensively to separate and identify *Escherichia coli* and *Salmonella* from foods. C. Blackburn et al., Separation and Detection of *Salmonellae* Using Immunomagnetic Particles, 5 Biofouling 143-156 (1991); P. M. Fratamico et al., Rapid Isolation of *Escherichia coli* O157:H7 from Enrichment Cultures of Foods Using an Immunomagnetic Separation Method, 9 Food Microbiol. 105-113 (1992); L. Krusell & N. Skovgaard, Evaluation of a New Semi-automated Screening Method for the Detection of *Salmonella* in Foods within 24 h, 20 Inter. J. Food Microbiol. 124-130 (1993); A. Lund et al., Rapid Isolation of K88$^+$ *Escherichia coli* by Using Immunomagnetic Particles, 26 J. Clin. Microbiol. 2572-2575 (1988); L. P. Mansfeild & S. J. Forsythe, Immunomagnetic Separation as an Alternative to Enrichment Broths for *Salmonella* Detection, 16 Letters Appl. Microbiol. 122-125 (1993); A. J. G. Okrend et al., Isolation of *Escherichia coli* O157:H7 Using O157 Specific Antibody Coated Magnetic Beads, 55 J. Food Prot. 214-217 (1992); E. Skjerve & Olsvic, Immunomagnetic Separation of *Salmonella* from Foods, 14 Inter. J. Food Microbiol. 11-18 (1991); D. J. Wright et al., Immunomagnetic Separation as a Sensitive Method for Isolating *Escherichia coli* O157 from Food Samples, 113 Epidemiol. Infect. 31-39 (1994). However, these methods involve either a preincubation or a subsequent incubation step (usually 18 to 24 hours) to increase the cell numbers for detection. Immunomagnetic capture greatly shortens *E. coli* and *Salmonella* testing, but long incubation times limit this method for predictive information. Immunocapture has also been used to quantitate *Bacillus anthracis* spores in soil samples using luminescent detection, J. G. Bruno & H. Yu, Immunomagnetic-electrochemiluminescent Detection of *Bacillus anthracis* Spores in Soil Matrices, 62 App. Environ. Microbiol. 3474-3476 (1996), but these efforts have led to tests that have a detection limit of $10^3$ cfu/ml.

Considerable progress in the development of biosensors for microbial detection has been achieved in the last decade.

These biosensors can be applied to medical, process control, and environmental fields. They must possess ideal features such as high specificity, simplicity, sensitivity, reliability, reproducibility, and speed. S. Y. Rabbany et al., Optical Immunosensors, 22 Crit. Rev. Biomed. Engin. 307-346 (1994). With the use of antibodies as the recognition element for specific capture, numerous applications have been developed for detection of pathogenic bacteria. M. R. Blake & B. C. Weimer, Immunomagnetic Detection of *Bacillus stearothermophilus* Spores in Food and Environmental Samples, 63 J. Appl. Environ. Microbiol. 1643-1646 (1997); A. Burkowski, Rapid Detection of Bacterial Surface Proteins Using an Enzyme-linked Immunosorbent Assay System, 34 J. Biochem. Biophys. Methods 69-71 (1997); S. A. Chen et al., A Rapid, Sensitive and Automated Method for Detection of *Salmonella* Species in Foods Using AG-9600 AmpliSensor Analyzer, 83 J. Appl. Microbiol. 314-321 (1997); L. A. Metherell et al., Rapid, Sensitive, Microbial Detection by Gene Amplification using Restriction Endonuclease Target Sequence, 11 Mol. Cell Probes 297-308 (1997); F. Roth et al., A New Multiantigen Immunoassay for the Quantification of IgG Antibodies to Capsular Polysaccharides of *Streptococcus pneumoniae*, 176 J. Inf. Dis. 526-529 (1997).

Methods for continuous flow immunoassay for rapid and sensitive detection of small molecules have been developed. For example, A. W. Kusterbeck et al., 135 J. Immunol. Methods 191-197 (1990), describes such a method in which detection of the antigen occurred within a matter of minutes. The assay is based on the binding of labeled antigen to an immobilized antibody, with subsequent displacement of the labeled antigen when antigen is present in the sample flow. Signal detection occurs downstream of the antigen recognition event.

In standard displacement flow immunoassays, the analyte of up to 1000 molecular weight in the sample creates an active dissociation of labeled antigens from an antigen binding site of an immobilized antibody, after which the labeled substance is measured downstream. W. A. Kaptein et al., On-line Flow Displacement Immunoassay for Fatty Acid-binding Protein, 217 J. Immunol. Methods 103-111 (1998), describes displacement in a flow system for detection of a small protein, cytoplasmic heart-type fatty acid-binding protein (15,000 molecular weight), a plasma marker for myocardial injury. This displacement system uses an inverse set-up: enzyme-labeled monoclonal antibodies are associated to immobilized antigen and are displaced by analyte in the sample.

F. Vianello et al., Continuous Flow Immunosensor for Atrazine Detection, 13 Biosens. Bioelectron. 45-53 (1998), describes detection of the hapten, atrazine, under continuous flow conditions using a micro-column containing immobilized monoclonal antibodies against atrazine and atrazine labeled with alkaline phosphatase. The equilibrium of the antibody-hapten system was achieved by continuous flow of the tracer (alkaline phosphatase-labeled atrazine) through the micro-column containing the immobilized antibodies. The activity of the tracer was monitored continuously downstream of the micro-column with an amperometric detector using p-hydroquinone phosphate as substrate. When pulses of unlabeled atrazine were added to the tracer flowing continuously through the micro-column, tracer bound to the antibody was displaced, with a consequent change in the detector signal.

C. H. Pollema & J. Ruzicka, Flow Injection Renewable Surface Immunoassay: A New Approach to Immunoanalysis with Fluorescence Detection, 66 Anal. Chem. 1825-1831 (1994), describes automatic heterogeneous immunoassays using a flow injection technique on a renewable surface. This assay relies on a minute amount of beads to form a reactive surface, which is interrogated by fluorescence spectrometry. Following the assay, the spent reactive surface is fluidically removed and replaced with a new layer of beads.

B. Mattiasson & M. P. Nandakumar, Binding Assays in Heterogeneous Media Using a Flow Injection System with an Expanded Micro-bed Adsorption Column, 8 Bioseparation 237-245 (1999), describes a competitive binding assay in a flow injection system wherein the adsorption step was carried out in an expanded bed column to increase the versatility of the assay an enable it to deal with samples containing particulate matter.

In view of the foregoing, it will be appreciated that compositions and methods for real time detection of selected antigens, such as contaminants in food and the environment, would be a significant advancement in the art.

BRIEF SUMMARY OF THE INVENTION

The present invention comprises compositions and methods for capture and detection of antigens from complex liquid samples within a matter of minutes and without the need for culturing of organisms.

An illustrative method according to the present invention for capturing and concentrating a selected antigen from an aqueous medium containing a mixture of antigens comprises:

(a) causing a first volume of the aqueous medium containing the mixture of antigens to flow through a module containing at least two antibody-bead conjugates, wherein each of the antibody-bead conjugates comprises a bead, a polymeric spacer covalently coupled to the bead, and an antibody covalently coupled to the polymeric spacer, wherein the antibody is configured for binding the selected antigen, at a first flow rate such that the antibody-bead conjugates form a fluidized bed and the selected antigen binds to the antibody-bead conjugates;

(b) washing the antibody-bead conjugates having the selected antigen bound thereto by causing a wash medium to flow through the module at a second flow rate such that the antibody-bead conjugates having the selected antigen bound thereto form a fluidized bed; and (c) holding the washed antibody-bead conjugates having the selected antigen bound thereto in a second volume of a second wash medium, wherein the second volume is smaller than the first volume.

Another illustrative method according to the present invention for detecting a selected antigen in aqueous medium containing a mixture of antigens comprises:

(a) causing the aqueous medium containing the mixture of antigens to flow through a module containing at least two antibody-bead conjugates, wherein each of the antibody-bead conjugates comprises a bead, a polymeric spacer covalently coupled to the bead, and an antibody covalently coupled to the polymeric spacer, wherein the antibody is configured for binding the selected antigen, at a first flow rate such that the antibody-bead conjugates form a fluidized bed and the selected antigen binds to the antibody-bead conjugates;

(b) washing the antibody-bead conjugates having the selected antigen bound thereto by causing a first wash medium to flow through the module at a second flow rate such that the antibody-bead conjugates having the selected antigen bound thereto form a fluidized bed; and (c) detecting the selected antigen bound to the antibody-bead conjugates by enzyme-linked immunosorbent assay.

An illustrative apparatus according to the present invention for use in capturing and detecting antigens comprises:

(a) a housing comprising a wall defining an interior chamber and comprising an inlet opening for conducting a liquid medium into the interior chamber and an outlet opening for conducting the liquid medium out of the interior chamber, wherein at least a portion of the wall is optically transparent;

(b) at least two antibody-bead conjugates disposed in the housing, each comprising a bead, a polymeric spacer covalently coupled to the bead, and an antibody coupled to the polymeric spacer;

(c) a liquid circulation circuit coupled to the housing for conducting the liquid medium into the interior chamber through the inlet opening and for conducting the liquid medium out of the interior chamber through the outlet opening at a selected flow rate; and (d) a photomultiplier tube mounted adjacent to the optically transparent portion of the wall for measuring photons produced in the interior chamber.

BRIEF DESCRIPTION OF THE SEVERAL VIEWS OF THE DRAWINGS

FIG. 1A illustrates specific capture of *B. stearothermophilus* spores from a mixed population containing equal amounts of *B. stearothermophilus* and *B. subtilis* spores, where *B. subtilis* spore counts in PBST are represented by the dotted bar, *B. stearothermophilus* spore counts in PBST are represented by the open bar, *B. subtilis* spore counts in milk are represented by the hatched bar, and *B. stearothermophilus* spore counts in milk are represented by the solid bar. FIG. 1B shows the concentration of spores in the wash: (□) *B. subtilis* in PBST, (◇) *B. stearothermophilus* in PBST, (○) *B. subtilis* in milk, and (Δ) *B. stearothermophilus* in milk.

FIG. 10 shows the beads settled by gravity at the bottom of the module, whereas FIG. 11 shows the positions of beads in a fluidized condition when liquid is passing through the module.

FIG. 17A shows results for ovalbumin (OVA). FIG. 17B shows results for *B. globigii* spores. FIG. 17C shows results for *E. coli* O157:H7.

DETAILED DESCRIPTION

Figure 2:
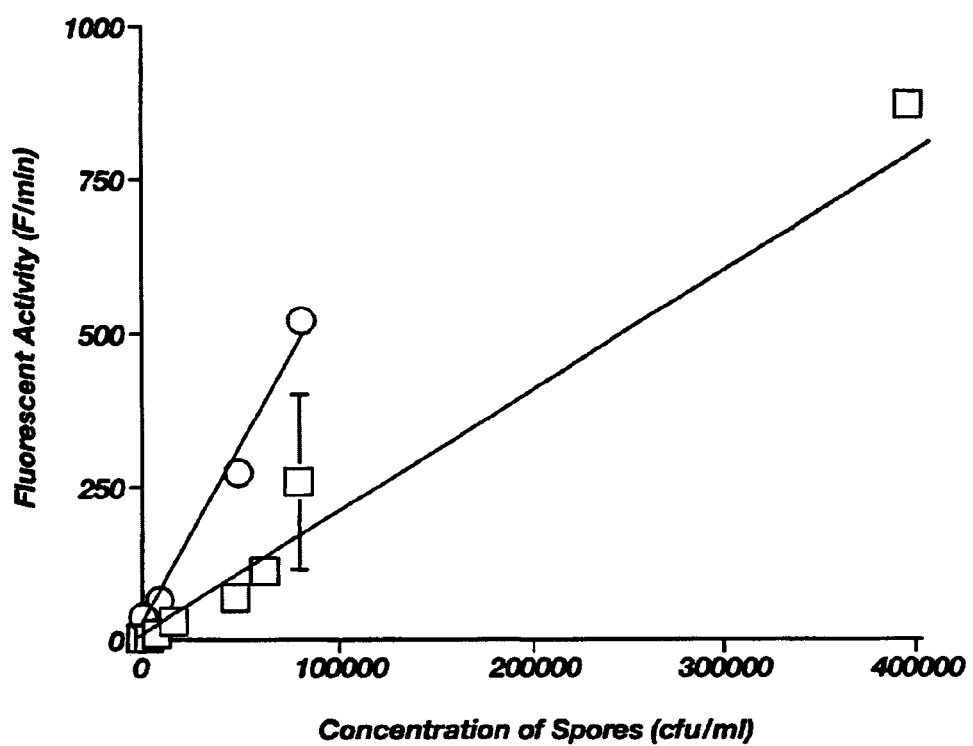
FIG. 2 shows fluorescence detection of captured *B. stearothermophilus* spores in skim milk by a biotin-avidin amplified sandwich ELISA using 3×10$^6$ (□) and 1.4×10$^7$ (○) immunomagnetic beads (IMBs); data points represent the mean of two replications, and error bars represent standard error of the means.

Before the present compositions and methods for real time detection of antigens are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the"

include plural referents unless the context clearly dictates otherwise. For example, reference to an apparatus containing "a bead" includes reference to two or more of such beads, reference to "a spacer" includes reference to one or more of such spacers, and reference to "an antibody" includes reference to two or more of such antibodies.

In describing and claiming the present invention, the following terminology will be used in accordance with the definitions set out herein.

As used herein, "antibody" means an immunoglobulin molecule that interacts and binds only with the antigen that induced its synthesis in lymphoid tissue and/or with antigens closely related to it. Included within this definition of antibody all antibody types, e.g., IgG, IgA, IgM, etc.; IgG subclasses, e.g., IgG1, IgG2, etc.; F(ab) fragments; F(ab')$_2$ fragments; F(ab') fragments; light chain dimers; single chain antibodies, and the like. This definition also includes antibodies that react with low and high affinity with an antigen. Further, such antibodies can be polyclonal or monoclonal.

As used herein, "cfu" means colony forming units.

As used herein, "PBS" means phosphate buffered saline: 0.01 M Na$_2$HPO$_4$, 0.15 M NaCl, pH 7.2.

As used herein, "PBST" means phosphate buffered saline containing 0.1% Tween 20.

As used herein, "BSA" means bovine serum albumin.

As used herein, "ELISA" means enzyme-linked immunosorbent assay.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

A fluidized or extended volume reactor filled with beads that have been modified with antibodies was developed for capturing antigens, such as specific microorganisms and biological molecules. The beads can be glass, ceramic, and the like, and are relatively large compared to those used in many antibody capture processes, typically in the range of about 1-7 millimeters (mm) in diameter. The antibodies are attached to the beads through a spacer. Typical spacers include polymers such as dextran, polyethylene glycol (PEG), and polyamino acids, such as polyserine and polythreonine.

Flow speed is typically about 0.2 to about 1.2 liters per minute. More typically, the flow speed is about 0.3 to about 0.7 liters per minute. The flow of the sample and wash solutions through the bead-containing module can be generated by use of vacuum pump, peristaltic pump, and other similar methods known in the art.

Detection of captured antigens can be by methods well known in the art, such as by surface ELISA using chemiluminescence (photometric), fluorescence, and spectrophotometric detection.

Luminescence is related to fluorescence in that both produce photons or light. In the case of fluorescence, however, energy must also be applied to excite the photons to escape the molecular structure. This is most often done with a laser and specific wavelengths of light. Luminescence does not require light input since chemicals or biological molecules provide the energy to excite the molecule. Unlike detection systems based on fluorescence, chemiluminescence methods do not require external light sources for excitation energy. The signals are generated internally as light-producing chemical reactions occur.

Detection of antigens according to the present invention typically involves a luminescence reaction, although fluorescence or colorimetric detection can also be used. The reporter enzyme used in the reaction determines which chemiluminescent substrate is employed. Horseradish peroxidase (HRP) and alkaline phosphatase (AP) are the two most common reporter enzymes. A common substrate is luminol (cyclic diacyl hydrazide), which is oxidized during the enzyme reaction. This oxidation converts the luminol substrate into an excited intermediate dianion. As the intermediate returns to its ground state, it emits light at a maximum of 425 nm. Another substrate is Lumigen APS-5 (Lumigen, Inc., Southfield, Mich.), which emits light at a maximum of 430 nm. Chemiluminescence is typically about 2 orders of magnitude more sensitive than fluorescence and more than 4 orders of magnitude more sensitive than chromogenic reactions. This sensitivity allows for lower detection limits in standard assays, such as ELISA.

EXAMPLE 1

Bacteria.

The bacteria used in the experiments described herein are described in Table 1. Commercial preparations of spores of *B. stearothermophilus* ATCC 10149, *B. cereus* ATCC 11778, and *B. subtilis* 6633 were purchased from Fisher Scientific, Pittsburgh, Pa. Viable spore numbers and germination estimates were obtained by plating on plate count agar (PCA) overnight at 65° C. and 30° C., respectively. All other spores except for *B. globigii* spores (Table 1) were prepared by spread-plating a single colony isolate on PCA and incubating the covered plate at 30° C. for approximately 2 weeks. Spores were swabbed from the surface of the agar and washed repeatedly in distilled water to remove water-soluble components. Spores were pelleted and separated from cell debris by centrifugation (1,500×g for 20 min at 4° C.; D. E. Gombas & R. F. Gomez, Sensitization of *Clostridium perfringens* Spores to Heat by Gamma Radiation, 36 Appl. Environ. Microbiol. 403-407 (1987)). Presence of spores was confirmed by heating to 80° C. for 15 min and then plating on PCA (G. H. Richardson, supra). Presence of an exosporium on the spore was tested by phase contrast microscopy with crystal violet staining (C. Du & K. Nickerson, *Bacillus thuringiensis* HD-73 Spores Have Surface-localized Cry Ac Toxin: Physiological and Pathogenic Consequences, 62 Appl. Environ. Microbiol. 3722-3726 (1996)). Spore titers were estimated by plating spores on plate count agar (PCA) and incubating overnight at 37° C. Based on these experiments, it was estimated that $10^{11}$ spores have a mass of 1 g.

TABLE 1

| Species | Inc. temp. (° C.) | Source | Exosporium |
| --- | --- | --- | --- |
| B. stearothermophilus | 65 | ATCC 10149[a] | − |
| B. cereus | 30 | ATCC 11778[a] | + |
| B. subtilis | 30 | ATCC 6633[a] | + |
| B. circulans | 30 | ATCC 4513[b] | − |
| B. coagulans | 30 | ATCC 7050[b] | − |

TABLE 1-continued

| Species | Inc. temp. (° C.) | Source | Exosporium |
|---|---|---|---|
| B. globigii | 30 | Dugway[c] | |
| B. licheniformis | 30 | OSU[d] | − |
| B. mascerans | 30 | OSU[d] | + |
| B. polymyxa | 30 | ATCC 842[b] | + |
| B. pumilus | 30 | OSU[d] | − |

[a]Purchased from Fisher Scientific, Pittsburgh, Pennsylvania.
[b]Purchased from American Type Culture Collection.
[c]Obtained from Dugway Proving Grounds (Tooele, Utah).
[d]Donated by Floyd Bodyfelt, Oregon State University.

EXAMPLE 2

Polyclonal Antibodies Production.

Polyclonal antibodies against B. cereus spores, B. subtilis spores, and B. stearothermophilus spores were made at the Utah State Biotechnology Center (Logan, Utah). BALB/c mice were injected in the intraperitoneal cavity with $1 \times 10^7$ cfu/ml cells or spores in sterile saline (0.5 ml) three times at 3-week intervals. E. Harlow & D. Lane, Antibodies, A Laboratory Manual (1988). Total ascites IgG was purified using a protein A/G column (Pierce Chemical, Rockford, Ill.). Antibodies were desalted and concentrated to 1 mg/ml in 0.1 M $NaPO_4$, pH 7.0 in a 30 kD Centricon filter (Amicon, Beverly, Mass.) at 4,500×g at 4° C.

Goat antibodies to *Bacillus globigii* spores were obtained from Dugway Proving Grounds (Tooele, Utah).

EXAMPLE 3

Monoclonal Antibody Production.

Monoclonal antibodies were produced against *B. stearothermophilus* by suspending the cells or spores in PBS to an optical density of 0.93 at 550 nm before intraperitoneally injecting female BALB/c mice with 0.250 mg (whole cell wet weight) without adjuvant. The mice were immunized 3 times at 3-week intervals. Seven days after the last immunization they were test bled, and the serum was titered by ELISA 3 days before fusion. Booster injections were administered by intraperitoneal injection with 0.1 mg cells in PBS. Fusion with a compatible murine myeloma cell line (P3X63-Ag8.653) was done in the presence of polyethylene glycol. Selection for hybrid cells was done in HAT medium. G. Kohler & C. Milstein, Continuous Cultures of Fused Cells Secreting Antibody of Pre-defined Specificity, 256 Nature 495-97 (1975) (hereby incorporated by reference). Positive colonies were determined by ELISA and were subcloned twice before freezing in liquid nitrogen.

EXAMPLE 4

Antibody Specificity.

Antibody specificity was tested by measuring the cross reactivity against *Bacillus* spores listed in Table 1 using a standard ELISA. A suspension of each spore type ($10^6$ cfu/ml), suspended in 50 mM $NaCO_3$ (pH 9.5), was non-specifically bound to wells of a microtiter plate for 12 h at 4° C. Wells containing spores were blocked with 2% bovine serum albumin (BSA) in PBS for 4 h at 25° C., and washed four times with PBS containing 0.1% Tween 20 (PBST). Anti-*B. stearothermophilus* antibodies (1:10,000 serum dilution in PBS) were added to wells, slowly agitated for 2 h at 25° C., and washed four times with PBST. Horseradish-peroxidase-labeled (HRP) anti-whole mouse IgG (Sigma Chemical Co., St. Louis, Mo.) was added to label anti-*B. stearothermophilus* antibodies for 2 h, then the wells were washed four times with PBST. O-Phenylenediamine dihydrochloride (Sigma) color development was measured using a b* color scale (blue to yellow) at 37° C. for 1 h in an automated reflectance calorimeter (Omnispec 4000 Bioactivity monitor; Wescor, Inc., Logan, Utah).

The anti-*B. stearothermophilus* antibodies did not cross react with any of the spore types tested (Table 1) including common aerobic spores found in raw foods. Lack of cross reactivity may be partly due to the absence of an exosporium on the *B. stearothermophilus* spores (Table 1). However, antibodies raised against *B. subtilis* and *B. cereus*, which have exosporia, were also specific for the injected spore types, suggesting that the surface antigens of the exosporia are sufficiently different as to not crossreact.

EXAMPLE 5

Antibody Attachment to Beads Via Biotin-Streptavidin.

Anti-*B. stearothermophilus* antibodies purified from total serum were biotinylated with NHS-LC-Biotin (Pierce Chemical, Rockford, Ill.). Efficiency of surface biotinylation was determined using the HABA assay (Pierce), except that the 2-mercaptoethanol step was omitted to avoid denaturing antibodies. This modified procedure gave the number of surface biotin moieties per antibody (Sigma Technical Support).

Biotinylated antibodies were coupled to streptavidin-bound magnetic beads (Dynabeads Streptavidin™, Lake Success, N.Y.) according to the supplier's directions.

EXAMPLE 6

Antibody Attachment to Bead Via Poly(threonine).

Sodium meta-periodate (5 mg) was used to oxidize carbohydrate moieties on the anti-*B. stearothermophilus* antibodies. G. T. Hermanson et al., Immobilized Affinity Ligand Techniques (1992) (hereby incorporated by reference). Sodium meta-periodate was removed after oxidation by washing five times with 0.1M $NaPO_4$, pH 7.0, in a 30 kD Centricon filter (4,500×g, 4° C.), and the oxidized antibodies were then immediately crosslinked to beads magnetic beads.

PolyThr (MW(vis) 12,100;Sigma Chemical, St. Louis, Mo.) was covalently coupled to 2.8-μm, tosyl-activated polystyrene Dynabeads (Dynal, Lake Success, N.Y.) in 50 mM borate buffer (pH 9.5) via the terminal amine as described by the product instructions. Four washes (three times for 10 min, and once for 30 min) with TBS buffer (pH 7.5) were used to block remaining tosyl-active sites. Adenine dihydrazine (ADH; 0.5 M in 0.1 M MES, pH 4.75; Sigma) was linked to the carboxy terminus of the bound PolyThr using an ethylene diamine carbodiimide mediated reaction (G. T. Hermanson et al., supra). Oxidized antibodies were mixed with the ADH-activated beads at room temperature for 12 h to allow crosslinking between the oxidized carbohydrate moiety of the IgG and the ADH terminus of the PolyThr spacer (G. T. Hermanson et al., supra). After crosslinking, the modified immunomagnetic beads (IMBs) were stored rotating (50 rpm) in PBST with 0.02% sodium azide at 40° C. until use.

EXAMPLE 7

Antibody Attachment to Bead Via Poly(serine).

In this example, the procedure of Example 6 was followed except that poly(serine) was substituted for poly(threonine).

EXAMPLE 8

Antibody Attachment to Bead Via Dextran.

Ceramic beads, 7 mm in diameter (Coors Ceramics Corp., Golden, Colo.), were washed in acidic methanol (HCl: methanol, 1:1) for 30 min at room temperature (RT) to strip the bead surface. The acidic methanol was poured off and the beads were rinsed several times with filtered water ($dH_2O$). The beads were further washed with concentrated sulfuric acid three times for 30 min, rinsed several times with $dH_2O$, and finally boiled in $dH_2O$ for 30 min to introduce hydroxyl groups onto the surface.

For silanization and crosslinking, beads were air dried, washed once in toluene and incubated in 3% 3-mercapto propyl trimethoxysilane (3% MTS in toluene) for 2 h at RT. Subsequently the beads were prepared for the addition of the crosslinker γ-maleimidobutyric acid N-hydroxy succinimide ester (GMBS; Sigma Chemicals, St. Louis, Mo.). Beads were washed twice in toluene to remove unbound MTS, air dried, and then incubated for 1 h at RT in 2 mM GMBS (in 100% ethanol). Finally, the beads were finally washed in 100% ethanol and then in PBS.

Dextran was used as a spacer between the crosslinker and the antibody. Sodium-m-periodate (Sigma Chemicals, St. Louis, Mo.) was used to oxidize the carbohydrate moieties on dextran (37.5 kDa, Sigma Chemicals, St. Louis, Mo.) for 3 h at RT while shaking. The salt was removed by washing four times with $dH_2O$ in 30 kDa Centricon filters (Amicon Inc., Beverly, Mass.) and immediately bound to the crosslinked beads. Adipic acid dihydride (ADH, 0.5 M in sodium phosphate, pH 7.2;Sigma Chemicals, St. Louis, Mo.) was then added to introduce an amine group to the bead surface, which could then react with the oxidized antibody. All unreacted sites were blocked with 1% Tris/BSA, pH 8.5.

EXAMPLE 9

In this example, anti-*B. stearothermophilus* antibodies were mixed with tosyl-activated magnetic beads (Dynal) according to the directions supplied with the beads such that the amine groups on the antibodies reacted with tosyl groups on the surface of the beads. The resulting modified beads contained the antibodies covalently bonded to the surface of the beads.

EXAMPLE 10

In this example, anti-Fc IgG was bound to magnetic beads according to the procedure of Example 9. After unbound IgG was washed off, the beads were reacted with anti-*B. stearothermophilus* antibodies such that the anti-Fc IgG bound the anti-*B. stearothermophilus* antibodies. The anti-Fc IgG thus formed a spacer between the magnetic beads and the anti-*B. stearothermophilus* antibodies.

EXAMPLE 11

In this example, anti-*B. stearothermophilus* antibodies attached to magnetic beads were tested for their ability to capture *B. stearothermophilus* spores. The antibody/bead conjugates (i.e., immunomagnetic beads or IMBs) were prepared according to the procedure of Examples 5, 6, 9, and 10. ELISA using HRP-labeled anti-IgG confirmed the presence of bound antibodies on the surfaces of the beads.

IMBs ($3 \times 10^6$ beads) were added to 1 ml of sample comprising $10^4$ or $10^6$ *B. stearothermophilus* spores in PBST. These mixtures were incubated for 30 min at 25° C. with rotation at 50 rpm. The IMBs were removed from the sample for 2 min with a magnetic particle concentrator (Dynal MPC-E-1) and washed four times with PBST to reduce IMB clumping and block spore adhesion to tube walls (E. Skjerve et al., Detection of *Listeria monocytogenes* in Foods by Immunomagnetic Separation, 56 Appl. Environ. Microbiol. 3478-3481 (1990)). After each wash, IMBs were transferred to a new microfuge tube. The presence of bound spores on IMBs was confirmed in duplicate by plate counts and phase contrast microscopy.

TABLE 2

| Attachment | Ab Modification | Ab Orientation | No. spores bound |
|---|---|---|---|
| Biotin-Streptavidin | NHS-LC-Biotinylation | Non-directional | $0^a$ $0^b$ |
| Ab-$NH_2$ to Tosyl groups on beads | None | Non-directional | $0^a$ $0^b$ |
| Anti-Fc IgG spacer | None | Directional | $0^a$ $0^b$ |
| PolyThr-ADH crosslinker | Carbohydrate oxidation | Directional | $160^a$ $3600^b$ |

$^a$Captured from $10^4$ spores/ml.
$^b$Captured from $10^6$ spores/ml.

These results show that of the conjugates tested only antibodies bound to beads through a poly(threonine) spacer were able to capture spores. These data suggest that spacer length and flexibility may play a role in the antibody-antigen interaction.

EXAMPLE 12

In this example, the procedure of Example 11 was followed except that conjugates containing poly(serine) (Example 7) and dextran (Example 8) spacers were substituted for the conjugate containing the poly(threonine) spacer. The results obtained with the poly(serine)—and dextran-containing conjugates were substantially similar to those obtained with the poly(threonine)—containing conjugate.

EXAMPLE 13

In this example, equal numbers of *B. subtilis* and *B. stearothermophilus* spores were mixed in PBST and in milk. Immunocapture using anti-*B. stearothermophilus* antibodies conjugated to magnetic beads was carried out according to the procedure of Example 11 except that samples containing milk were given 5 minutes to separate the beads from the medium using the magnetic particle concentrator due to the slower bead recovery. After capture of spores using the immunomagnetic bead conjugate, the conjugates were washed with PBST and the wash supernates were plated on PCA. This washing procedure was repeated three times such that a total of four wash supernates were assayed.

FIG. 1A shows the conjugate specifically captured *B. stearothermophilus* spores from PBST and milk containing equal numbers of *B. stearothermophilus* and *B. subtilis* spores. FIG. 1B shows that about 99% of non-specifically bound spores were removed from the conjugate with each wash, leaving *B. stearothermophilus* spores captured by the conjugate after four washes.

The anti-*B. stearothermophilus* antibodies did not cross react with any of the spore types tested (Table 1) including common aerobic spores found in raw foods.

EXAMPLE 14

Product Testing.

In this example, muck clay, ground pepper, skim milk, whole milk, and acidic sandy soil were tested for detection of bacterial spores. Fluid products were tested with no modification. Powdered products were suspended at 1 g/ml. Anti-*B. stearothermophilus* antibody conjugated beads prepared according to the procedure of Example 6 were added to 1 ml of each product and mixed gently at 25° C. Bound spores were quantitated using calorimetric (as described above) or fluorescence detection. For fluorescence detection, spores bound to IMBs were labeled with secondary biotinylated anti-*B. stearothermophilus* antibodies. The IMBs were then washed with PBST and resuspended in an ABC-alkaline phosphatase complex solution (Vector Laboratories, Inc., Burlingame, Calif.) for 30 min. The IMBs were washed three times with PBST and resuspended in 100 µl of 0.2 M Tris buffer containing 0.1% BSA (pH 8.5) to remove unbound enzyme complex. A 40-µl suspension of the IMBs was added to 3 ml of Fluorophos substrate (Advanced Instruments, Norwood, Mass.) and fluorescence monitored for 2 min at 38° C. in a Fluorophos FLM200 fluorometer (Advanced Instruments, Norwood, Mass.).

As shown in FIG. 2, using immunocapture-sandwich ELISA, spores in UHT skim milk were quantified down to $8 \times 10^3$ cfu/ml in 2 h with no pre-enrichment steps and no sample preparation. Increasing the number of beads in the assay increased the fluorescence activity, suggesting that this could further increase the assay sensitivity (P. M. Fratamico et al., supra; E. Skjerve et al., supra).

Figure 3:
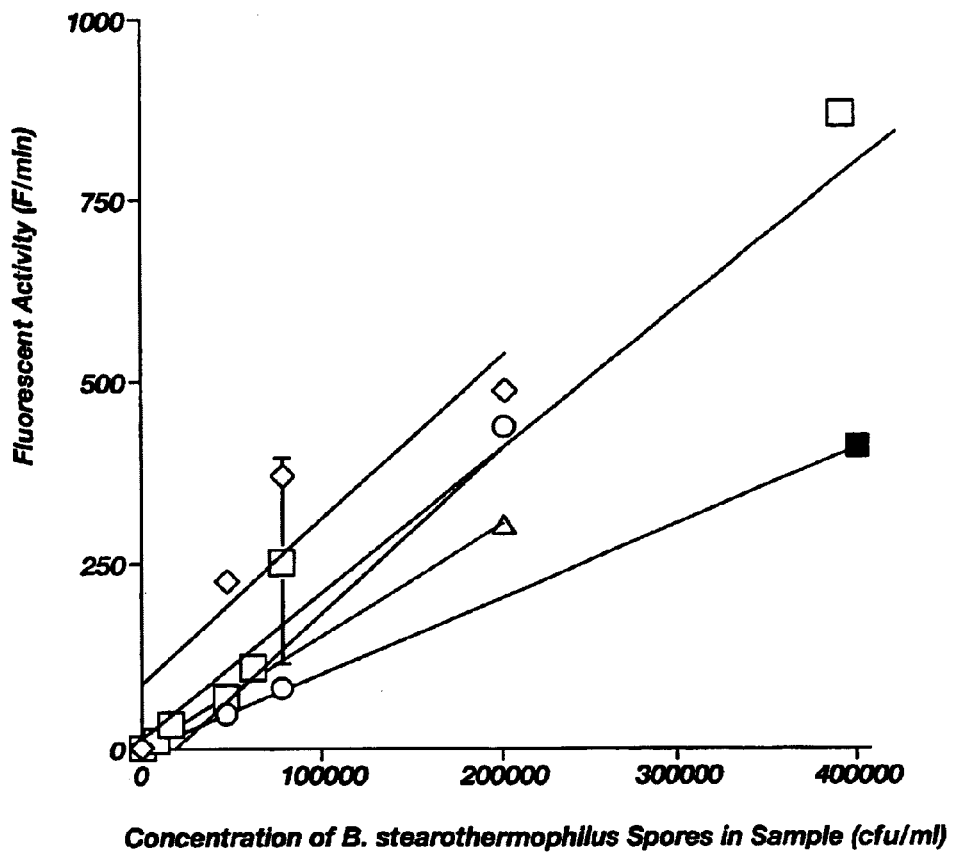
FIG. 3 shows fluorescence detection of captured *B. stearothermophilus* spores from various food and environmental samples using 3×10$^6$ IMBs: (◇) muck clay, $R^2$=0.82; (○) pepper, $R^2$=0.96; (□) skim milk, $R^2$=0.99; (Δ) whole milk; (■) acidic sandy soil (pH 3.7); data points represent the mean of two replications, and error bars represent standard error of the means.

The slope of the generated curves was similar for all samples tested, indicating that sample background did not grossly influence antigen binding (FIG. 3). Therefore, approximate spore loads can be obtained without calibrating the assay to each product. Foods containing fat, such as raw whole milk, required a longer time for separation of the IMBs and gentle removal of supernate to avoid trapping the beads in the fat and removing them with the supernate. Separation of IMBs from fatty products required 5 min rather than the 2 min used for nonfat samples. Soil samples containing a high percentage of iron fines interfered with bead recovery, although other soil types tested did not. These data support the use of this assay to test for *B. stearothermophilus* spores in food and environmental sample.

Since the assay has been designed to be used with raw ingredients that may vary in temperature, the ability of the IMBs to capture *B. stearothermophilus* spores at temperatures ranging from 4° C. to 55° C. was tested. IMBs were added to 1 ml UHT skim milk containing $5 \times 10^4$ *B. stearothermophilus* spores and incubated between 4° C. to 55° C. while rotating (50 rpm) for 30 min. The IMB were washed four times with PBST, plated on PCA, and incubated overnight at 65° C. *B. stearothermophilus* colonies were counted to quantitate bound spores. Regardless of the temperature of the sample, the number of spores captured from UHT skim milk containing $5 \times 10^4$ *B. stearothermophilus* spores did not vary significantly. This means that sample preparation time can be reduced. These data suggest that this approach is over 100 times more sensitive than the only other rapid spore assay (Y. H. Chang & P. M. Foegeding, supra), is about 10 times faster than any spore assay with equivalent sensitivity (G. H. Richardson, supra), and can be used to quantitate a single species of spore in a mixed spore population in chemically complex backgrounds.

Figure 4:
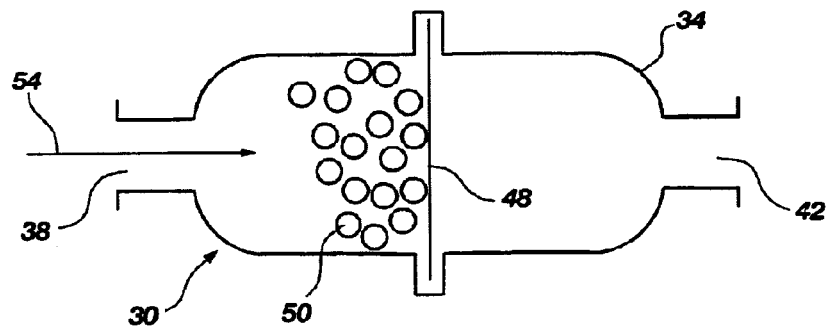
FIG. 4 shows a schematic representation of an illustrative module for use in detecting antigens according to the present invention.
Figure 5:
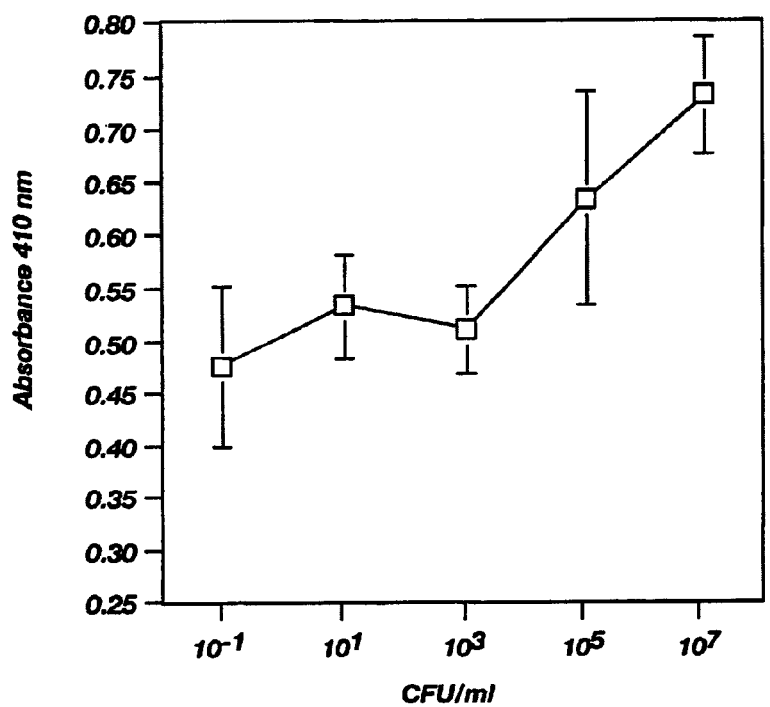
FIG. 5 shows immunoflow (2 L/min) detection of *B. globigii* spores in 0.1 M phosphate buffer (pH 7.2, $R^2$=0.9; slope=0.03).
Figure 6:
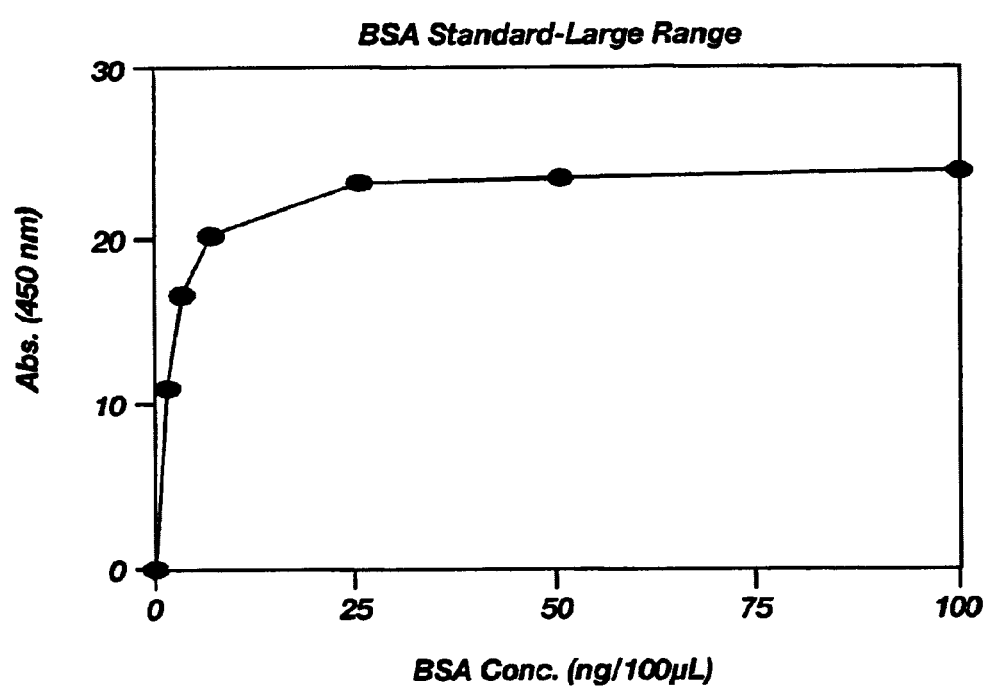
FIG. 6 shows a bovine serum albumin (BSA) standard curve at the range of 1.5-100 ng/μl; each point is the average absorbance (450 nm) in triplicate, and PBST (0.2% Tween 20) was the blocking reagent to block the nonspecific binding sites.
Figure 7:
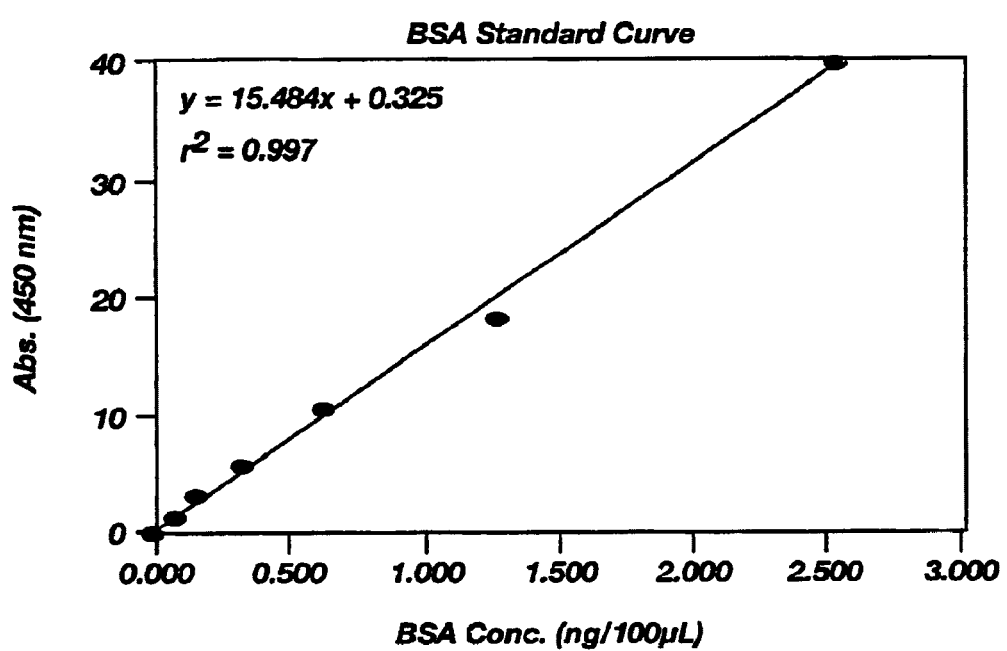
FIG. 7 shows a BSA standard curve at the range of 0.075-2.5 ng/μl; each point is the average absorbance (450 nm) in triplicate; PBST (0.2% Tween 20) was the blocking reagent.
Figure 8:
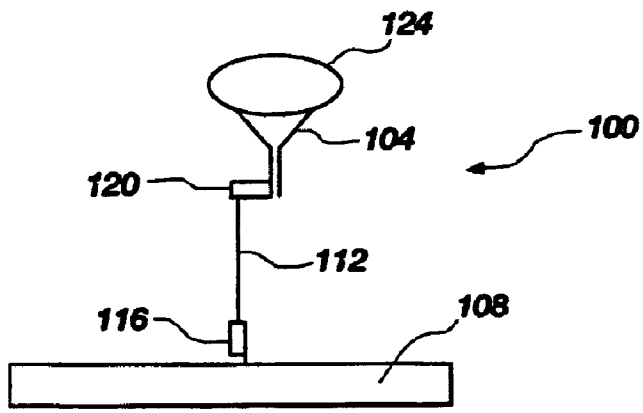
FIG. 8 shows a schematic diagram of an illustrative composition for use in binding antigens to a solid support according to the present invention.
Figure 9:
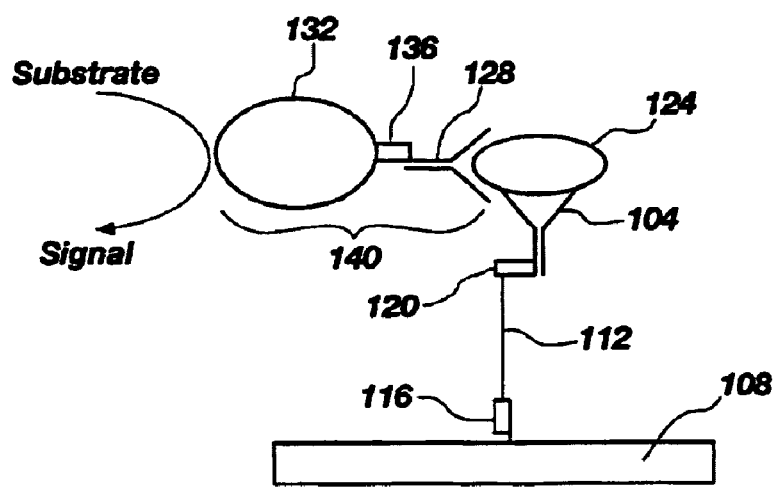
FIG. 9 shows a schematic diagram of detection of antigens captured with the composition of FIG. 8.

While detection of spores was achieved with immunomagnetic beads, it was believed that sensitivity and efficiency could be improved by using a fluidized bed capture system. Hence, the capture step was fluidized by immobilizing antibodies onto larger beads ranging is size from 1-7 mm. Use of a fluidized bed module (FIG. 4) further increased the sensitivity of the assay to less than a single cell per ml of liquid and allowed the assay to be done without pre-incubation and to obtain a finished result within 30 min in all the samples tested (FIG. 5). FIG. 4 shows a schematic representation of an illustrative module 30 comprising a housing 34 having an inlet opening 38 for flow of a liquid medium to be tested into the module. A plate 46 having holes therein to permit flow of the liquid through the module is placed with the plane of the plate generally perpendicular to the direction of flow of the liquid. The beads 50 are placed upstream of the plate. Arrow 54 shows the direction of flow of liquid through the module. The size of the holes in the plate is selected to be smaller than the size of the beads such that the beads cannot pass through the outflow opening 42. In an illustrative embodiment of the module, the holes in the plate were 3 mm in diameter, and the beads were 7 mm in diameter. The housing and plate should be constructed of materials, such as stainless steel and high durability plastics, having high durability and compatibility with liquids of various types.

EXAMPLE 15

In this example, 0.1 M phosphate buffer, pH 7.2, containing various concentrations of *B. globigii* spores was passed through an immunoflow module containing 7 mm ceramic beads having anti-*B. globigii* antibodies conjugated thereto according to the procedure of Example 6. The buffer was pumped through the module at 2 L/min. After capture of the spores, all of the beads were removed from the module, and a solid phase ELISA using biotinylated anti-*B. globigii* antibodies to amplify the signal was performed according to the procedure of Blake & Weimer, supra. The signal was read at 410 nm in a Biospec 1601 (Shimadzu Scientific Corp., Columbia, Md.) and compared to a standard curve. FIG. 5 shows that spores could easily be detected at concentration of less than 1 cfu/ml.

In a companion experiment, the following foods were tested for the presence of *B. globigii* spores by immunoflow capture: raw whole milk, skim milk, raw hamburger, canned green beans, canned corn, canned peas, canned carrots, canned mixed vegetables, canned spinach, beer, fermented sausage, Vienna sausage, raw chicken, canned chicken, canned pork and beans, canned kidney beans, fresh sliced mushrooms, and canned tomato sauce. Fluid products were tested without modification. Other products were dissolved or suspended at 1 g/ml. Fifty ml of product was pumped through the module at a rate of 2.5 L/min. Bound spores were quantitated using fluorescence detection as described above. *B. globigii* spores were detected in each of these foods at a concentration of 1 spore/ml.

This is a significant improvement over prior results and provided a method for increasing the sample size that could be used. Use of immunoflow at 2-4 L/min allowed detection in less time and in the presence of fat or protein that interfered with immunomagnetic detection and some foods. A characteristic dip at $10^3$ spores/ml was found, which is commonly observed. The cause for this deviation is unknown but is linked to the lower flow rate used, since this dip is not noticeable at flow rates>4L/min. The dynamic range is at least nine decades, suggesting this module will not easily be overloaded in the field.

EXAMPLE 16

In this example, the procedure of Example 15 was carried out except that river water (pH 8.5) with added *B. globigii* spores ($10^3$ spores/ml) was pumped through the module at a flow rate from 1 to 4 L/min for times ranging from 1 to 180 minutes. Detection and spore capture increased as the flow rate increased, with the maximum detection at 15 minutes and a flow rate of 4 L/min. Detection decreased as the flow rate decreased and as the flow time increased. These data suggest a complex interaction between the capture surface and the spore is occurring, but that it is not matrix dependent. Similar results were observed with detection of *B. globigii* spores in PBS and penicillin in milk at 114 L/min. Additionally, the results obtained with penicillin detection suggests that the range of flow rates for capture and detection is large, at least 1-114 L/min.

EXAMPLE 17

To demonstrate the use of immunoflow with small protein targets, BSA detection was done using immunoflow with 5 mm glass beads modified with dextran and anti-BSA antibodies and a flow rate of 2 L/min. The assay detected BSA over a broad range (FIG. 6), and had a lower detection limit of at least 0.075 ng/ml without the avidin/biotin complex for amplification (FIG. 7). These data confirm the use of immunoflow detection for use with chemicals (penicillin), small proteins (BSA), and microbes (*Bacillus* spores) at flow rates varying from 1-114 L/min.

FIG. 8 shows an illustrative embodiment of the present invention for capturing and detecting an antigen from a sample. This illustrative composition 100 comprises an antibody 104 coupled to the surface of a solid support, for example, a bead 108. The antibody 104 is coupled to the bead 108 by means of a spacer 112. As described above, spacers can include dextran, polythreonine, polyserine, polyethylene glycol, biotin/avidin linkages, and the like. The spacer 112 is coupled to the surface of the bead 108 by a chemical linker 116, and the antibody 104 is also coupled to the spacer 112 by a chemical linker 120. A bacterium 124 captured by the composition 100 is shown bound to the antibody 104.

FIG. 9 shows detection of the bacterium 124 captured as illustrated in FIG. 8. Detection is by a high flow rate solid phase ELISA according to methods well known in the art. A secondary antibody 128 is linked to an enzyme 132 by means of a chemical linker 136 for providing an amplification complex 140 for providing a detectable signal when a suitable substrate is placed in contact with the amplification complex 140. Illustrative substrates that can be used in accordance with the present invention include those that yield visual, calorimetric, luminescent, and fluorescent signals upon digestion of the substrate by the enzyme.

Methods for detecting antibody/antigen or immune complexes are well known in the art. The present invention can be modified by one skilled in the art to accommodate the various detection methods known in the art. The particular detection method chosen by one skilled in the art depends on several factors, including the amount of sample available, the type of sample, the stability of the sample, the stability of the antigen, and the affinity between the antibody and antigen.

While these techniques are well known in the art, examples of a few of the detection methods that could be used to practice the present invention are briefly described below.

There are many types of immunoassays known in the art. For example, a common type of immunoassay is a non-competitive sandwich or capture assay, such as enzyme-linked immunosorbent assays (ELISA). In a non-competitive capture ELISA, unlabeled antigen is captured by an antibody bound to a solid support, such as the surface of the bead as illustrated in FIG. 8. After the immune complexes have formed, excess sample is removed and the bead is washed to remove nonspecifically bound antigen. If the concentration of the antigen in the sample is sufficiently dilute, however, it may not be necessary to remove nonspecifically bound antigens because such antigens are present in such low amounts. The immune complexes are then reacted with an appropriate enzyme-labeled antibody (secondary antibody), which recognizes the same or a different epitope on the antigen as the primary antibody. The secondary antibody reacts with antigens in the immune complexes. After a second wash step, the enzyme substrate is added. The enzyme linked to the secondary antibody catalyzes a reaction that converts the substrate into a product. Hence, enzyme activity is directly proportional to the amount of antigen in the biological sample. D. M. Kemeny & S. J. Challacombe, ELISA and Other Solid Phase Immunoassays (1988). Illustratively, the product is fluorescent or luminescent, which can be measured using technology and equipment well known in the art. It is also possible to use reaction schemes that result in a colored product, which can be measured spectrophotometrically, but such calorimetric reactions are not preferred.

Typical enzymes that can be linked to secondary antibodies include horseradish peroxidase, glucose oxidase, glucose-6-phosphate dehydrogenase, alkaline phosphatase, β-galactosidase, and urease. Secondary antigen-specific antibodies linked to various enzymes are commercially available from, for example, Sigma Chemical Co. and Amersham Life Sciences (Arlington Heights, Ill.).

Fluorescence immunoassays can also be used when practicing the method of the present invention. Fluorescence immunoassays are similar to ELISAs except the enzyme is substituted for fluorescent compounds called fluorophores or fluorochromes. These compounds have the ability to absorb energy from incident light and emit the energy as light of a longer wavelength and lower energy. Fluorescein and rhodamine, usually in the form of isothiocyanates that can be readily coupled to antigens and antibodies, are most commonly used in the art. D. P. Stites et al., Basic and Clinical Immunology (1994). Fluorescein absorbs light of 490 to 495 nm in wavelength and emits light at 520 nm in wavelength. Tetramethylrhodamine absorbs light of 550 nm in wavelength and emits light of 580 nm in wavelength. Illustrative fluorescence-based detection methods include ELF-97 alkaline phosphatase substrate (Molecular Probes Inc., Eugene, Oreg.); PBXL-1 and PBXL-3 (phycobilisomes conjugated to streptavidin) (Martek Biosciences Corp., Columbia, Md.); FITC and Texas Red labeled goat anti-human IgG (Jackson ImmunoResearch Laboratories, Inc., West Grove, Pa.); and B-Phycoerythrin and R-Phycoerythrin conjugated to streptavidin (Molecular Probes Inc.). ELF-97 is a nonfluorescent chemical that is digested by alkaline phosphatase to form a fluorescent molecule. Because of turn over of the alkaline phosphatase, use of the ELF-97 substrate results in signal amplification. Fluorescent molecules attached to secondary antibodies do not exhibit this amplification.

Phycobiliproteins isolated from algae, porphyrins, and chlorophylls, which all fluoresce at about 600 nm, are also being used in the art. I. Hemmila, Fluoroimmunoassays and Immunofluorometric Assays, 31 Clin. Chem. 359 (1985); U.S. Pat. No. 4,542,104. Phycobiliproteins and derivatives thereof are commercially available under the names R-phycoerythrin (PE) and Quantum Red™ from, for example, Sigma Chemical Co.

In addition, Cy-conjugated secondary antibodies and antigens are useful in immunoassays and are commercially available. Cy-3, for example, is maximally excited at 554 nm and emits light of between 568 and 574 nm. Cy-3 is more hydrophilic than other fluorophores and thus has less of a tendency to bind nonspecifically or aggregate. Cy-conjugated compounds are commercially available from Amersham Life Sciences.

Illustrative luminescence-based detection methods include CSPD and CDP star alkaline phosphatase substrates (Roche Molecular Biochemicals); and SuperSignal® horseradish peroxidase substrate (Pierce Chemical Co., Rockford, Ill.).

Chemiluminescence, electroluminescence, and electrochemiluminescence (ECL) detection methods are also attractive means for quantifying antigens and antibodies in a sample. Luminescent compounds have the ability to absorb energy, which is released in the form of visible light upon excitation. In chemiluminescence, the excitation source is a chemical reaction; in electroluminescence the excitation source is an electric field; and in ECL an electric field induces a luminescent chemical reaction.

Molecules used with ECL detection methods generally comprise an organic ligand and a transition metal. The organic ligand forms a chelate with one or more transition metal atoms forming an organometallic complex. Various organometallic and transition metal-organic ligand complexes have been used as ECL labels for detecting and quantifying analytes in biological samples. Due to their thermal, chemical, and photochemical stability, their intense emissions and long emission lifetimes, ruthenium, osmium, rhenium, iridium, and rhodium transition metals are favored in the art. The types of organic ligands are numerous and include anthracene and polypyridyl molecules and heterocyclic organic compounds. For example, bipyridyl, bipyrazyl, terpyridyl, and phenanthrolyl, and derivatives thereof, are common organic ligands in the art. A common organometallic complex used in the art includes tris-bipyridine ruthenium (II), commercially available from IGEN, Inc. (Rockville, Md.) and Sigma Chemical Co.

Advantageously, ECL can be performed under aqueous conditions and under physiological pH, thus minimizing biological sample handling. J. K. Leland et al., Electrogenerated Chemiluminescence: An Oxidative-Reduction Type ECL Reactions Sequence Using Triprophyl Amine, 137 J. Electrochemical Soc. 3127-3131 (1990); WO 90/05296; U.S. Pat. No. 5,541,113. Moreover, the luminescence of these compounds may be enhanced by the addition of various cofactors, such as amines.

In practice, a tris-bipyridine ruthenium (II) complex, for example, may be attached to a secondary antibody using strategies well known in the art, including attachment to lysine amino groups, cysteine sulfhydryl groups, and histidine imidazole groups. After washing nonspecific binding complexes, the tris-bipyridine ruthenium (II) complex would be excited by chemical, photochemical, and electrochemical excitation means, such as by applying current to the bead. E.g., WO 86/02734. The excitation would result in a double oxidation reaction of the tris-bipyridine ruthenium (II) complex, resulting in luminescence that could be detected by, for example, a photomultiplier tube. Instruments for detecting luminescence are well known in the art and are commercially available, for example, from IGEN, Inc.

Figures 10, 11:
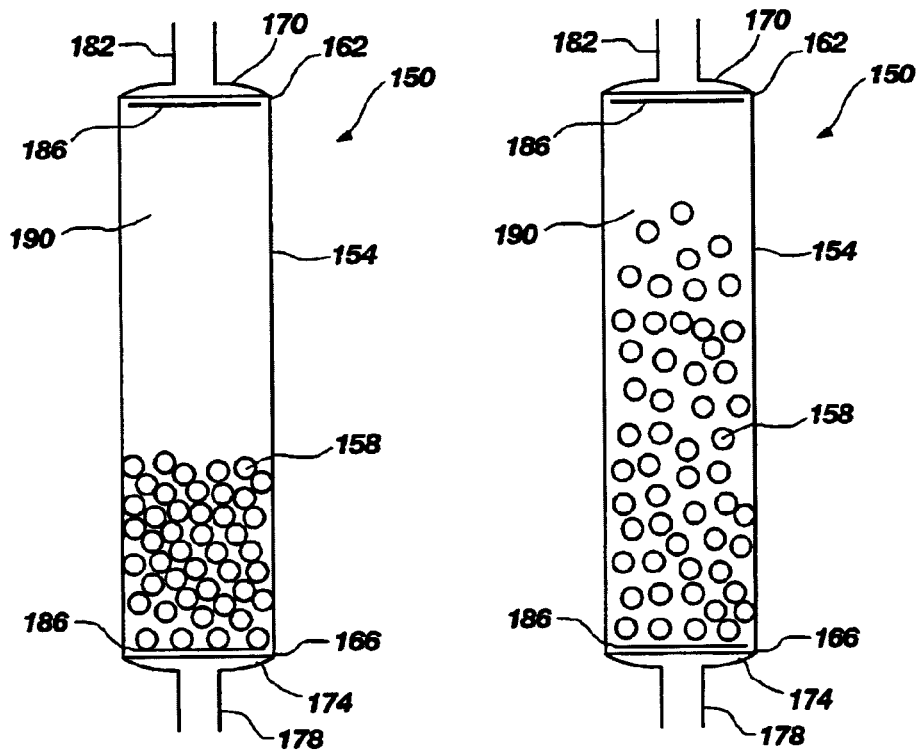
FIGS. 10 and 11 show a module or bead container for holding the bead-bound antibodies for capturing and detecting antigens according to the present invention.

FIGS. 10 and 11 show a module 150 or bead holder into which the bead-bound antibodies are placed. The module comprises a transparent plastic tube body 154 that holds the beads 158 in a column format. The tube body comprises a top end 162 and a bottom end 166. A top cap 170 is disposed on the top end of the tube body, and a bottom cap 174 is disposed on the bottom end of the tube body. The bottom cap 174 comprises an inlet 178 for permitting liquid to enter the module, and the top cap 170 comprises an outlet 182 for permitting liquid to exit the module. The outlet 182 and the inlet 178 are configured for being received in the lumen of tubing for linking the module to liquid handling systems, as will be described in more detail momentarily. A porous screen 186 is disposed in the cavity 190 formed by the tube body and the top cap and the bottom cap adjacent to both the top end 162 and the bottom end 166 of the tube body. These porous screens 186 are configured to permit liquid to pass therethrough while retaining the beads 158 in the cavity 190.

Once the antibodies have been attached to beads as described herein, the beads are loaded into the module. Typically, 10 to 280 beads are used. Illustratively, 55 beads (2 g of 3 mm diameter beads) may be used.

Figure 12:
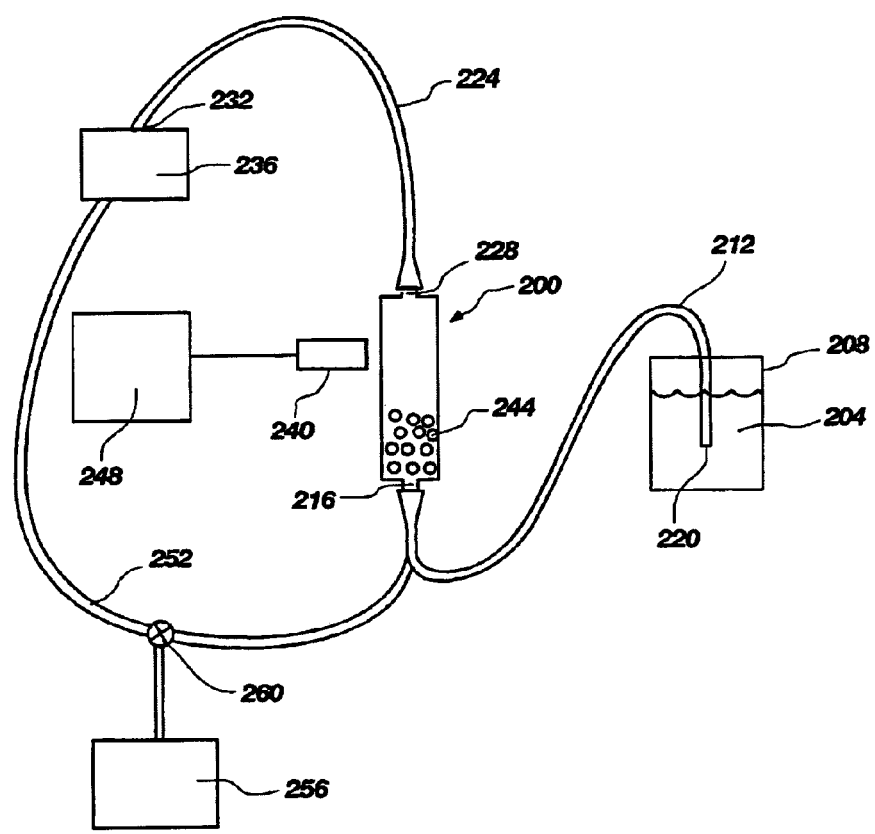
FIG. 12 shows a schematic diagram of an illustrative apparatus for use in detecting antigens according to the present invention.

FIG. 12 shows the module 200, as described above, connected to components of a system for use in detecting an antigen in a sample. The sample 204 is contained in a vessel 208. A section of tubing 212 is coupled to the inlet 216 of the module 200, and the distal end 220 of the tubing 212 is placed in the sample 204. Another section of tubing 224 is coupled to the outlet 228 of the module 200, and the distal end 232 of the tubing 224 is coupled to a vacuum pump 236. A photomultiplier tube 240 or PMT is mounted adjacent to the module 200 such that when the beads are at rest, the PMT 240 is above the level of the beads 244. The PMT 240 is coupled to signal detection electronics 248 for detecting and counting signals produced by the PMT 240.

The apparatus of FIG. 12 is used by placing a sample 204 in the vessel 208, and then causing the vacuum pump 236 to draw a vacuum through the sections of tubing 224 and 212 and the module 200, thereby drawing the sample liquid 204 through tubing 212, through the module 200, and through tubing 224. The sample can be recirculated through the module through another section of tubing 252 or can be collected in a trap 256. A valve 260 in tubing line 252 controls whether the sample is recirculated or trapped. The flow of the sample through the beads 244 causes the beads to be fluidized in the cavity of the module. A portion of the antigens contained in the sample are bound by bead-bound antibodies in the module. After capture of the antigens, the beads can be washed by placing the distal end 220 of tubing 212 in another vessel containing a wash solution. Operation of the vacuum pump draws the wash solution through the beads for washing away debris. After washing of the beads, enzyme-labeled secondary antibodies are drawn through the module in a similar manner. The enzyme-labeled secondary antibodies bind to the captured antigens. Another washing step can then be carried out. Next, a solution containing a substrate for the enzyme is passed through the module such that the substrate comes in contact with the enzyme. The substrate is digested by the enzyme to result in a detectable signal, such as a luminescent signal as described above. At this point, the vacuum pump is turned off such that the beads in the module settle by gravity to the bottom of the module. Once this has occurred, the PMT is activated for detecting the signal, such as a luminescent signal. Detection of the luminescent signal by the PMT results in the production of an electronic signal, which is transmitted to the signal detection electronics apparatus for detection, counting, and analysis of the electronic signals. The number of electronic signals detected and counted by the signal detection electronics is proportional to the number of antigens captured in the module.

Figure 13:
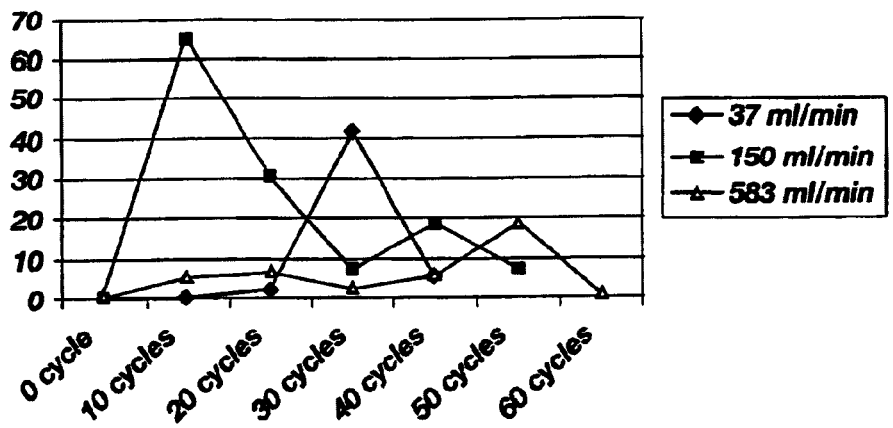
FIG. 13. shows capture of *E. coli* O157:H7 from buffer on the surface of bead-bound antibodies.
Figure 14:
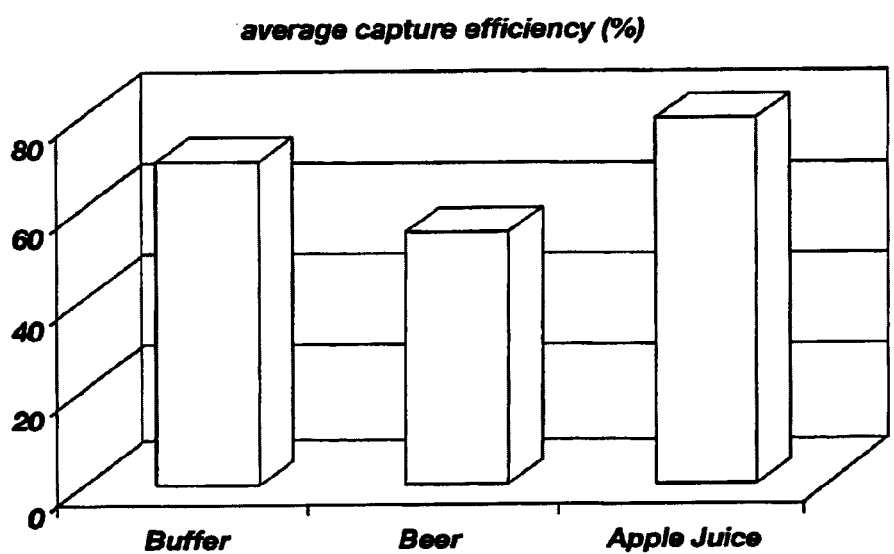
FIG. 14 shows the average capture efficiency *E. coli* O157:H7 from buffer, beer, and apple juice using bead-bound antibodies.

Illustratively, the vacuum pump can be set to draw a vacuum of 2 to 5 inches of mercury. It has been determined through experience that a setting of 5 inches of mercury is satisfactory for capturing a target antigen on the surface of beads. This amount of vacuum fluidizes the bead bed, and permits capture of sufficient antigen for detection in about 5 minutes with 50 ml samples. FIG. 13 shows capture of *E. coli* O157:H7 from buffer on the bead surface with fluorescently labeled cells. Each flow rate has an optimum cycling time for achieving capture. A flow rate of about 150 ml/min is convenient for use with a 50 ml sample. The data of FIG. 13 were verified by doing plate counts, according to methods well known in the art, in various foods in the same experimental design, but looking at the remaining fluid in the tube at the maximum capture settings for 150 ml/min (FIG. 14). In each food type, the fluidized bed of beads with anti-*E. coli* O157:H7 attached thereto captured the cells during the sampling time at 150 ml/minute. In each sample type, the cells were specifically captured onto the bead surface. Comparison of FIGS. 13 and 14 indicates that the beads capture the cells at approximately the same efficiency in both methods. Therefore, the cells were specifically captured by the antibody-modified beads.

Once the target antigen is captured and the debris is washed away, the other reagents are added in the same manner, i.e., they are caused to flow into the module with the vacuum of the same setting. The antibodies bind the antigens, and any excess is washed away from the beads.

Figure 15:
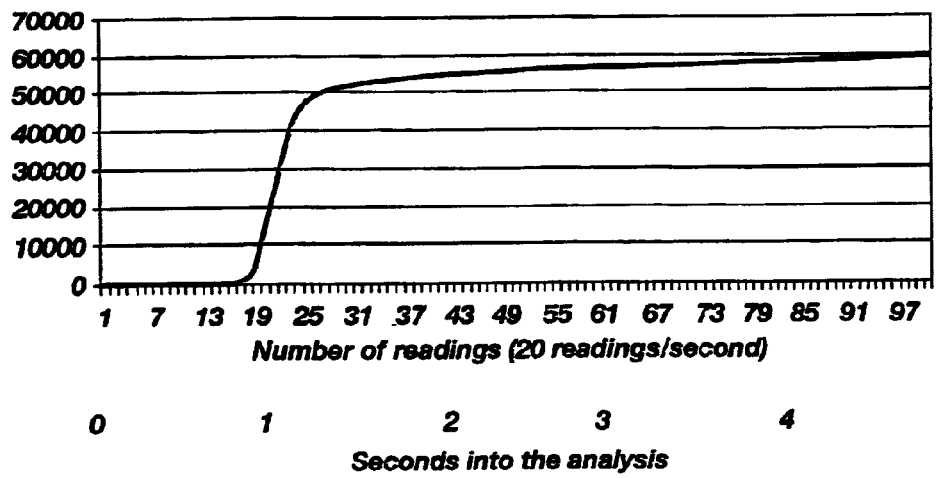
FIG. 15 shows signal detection from the surface of beads.

Next, the substrate, such as Lumigen APS-5, is added and then held in the module as the signal develops due to the amplification complex (FIG. 15). This may be done with many types of molecules, but horseradish peroxidase and alkaline phosphatase are especially convenient. The signal is generated and is stable within about 3 minutes. The useful portions of the curve are shown in the circles (FIG. 15). The analysis can be done with a running slope or an endpoint. The information needed to calculate the running slope is available within the first 2 seconds of the curve.

Figure 16:
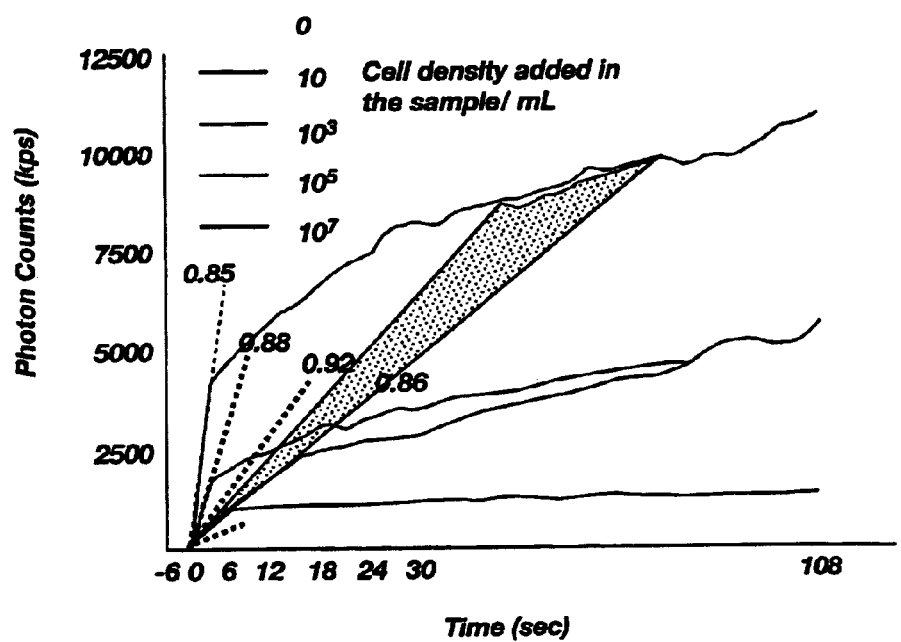
FIG. 16 shows determination of cell density by the method of the present invention.

Once this curve is generated, it is used to determine the amount of bacteria captured onto the bead surface (FIG. 16). Comparison of the initial slopes or the endpoint allow the final result to be determined. Based on these calculations, the cell density in the original sample is determined and reported. Use of the initial slopes is more discriminating, but the endpoint is adequate for rough estimation of the mid-range concentrations.

The signal is detected with a photon-counting PMT specific for luminescence, for example a Hamamatsu model H7360.

Table 3 shows the results of detection of *E. coli* O157:H7 by the procedure of the present invention as compared to the results achieved with known commercial tests. In all cases, the present invention, termed ImmunoFlow, detected the added organism in each food within 30 minutes without the need for culturing the organism. The ImmunoFlow tests were done without pre-enrichment, whereas the immunoprecipitation and lateral flow ELISA and all experiments with bean sprouts were done with 24 hr of pre-enrichment.

TABLE 3

| Food type | ImmunoFlow | BAM | Immunoprecipitation | Lateral Flow ELISA |
|---|---|---|---|---|
| Apple juice control | − | − | − | − |
| Apple juice | + | + | + | + |
| Beer control | − | − | − | − |
| Beer | + | + | + | + |
| Hamburger control | − | − | − | − |
| Hamburger | + | + | + | + |
| Bean sprouts | + | + | + | + |

EXAMPLE 18

In a 1-liter flask, 94 ml of double-distilled water and 1.88 g of dextran (Sigma, St. Louis, Mo.) were combined and mixed by swirling the flask until all of the dextran was solubilized. The flask was then wrapped in aluminum foil and 3.12 g of $NaIO_4$ was added. The flask was then capped with foil and placed on a shaker at low speed for 1 hour. Next, the flask was removed from the shaker and 125 g of APTES glass beads (3 mm diameter) was added. The flask was then returned to the shaker for 1 hour of agitation at low speed. Following agitation, the beads were removed from the flask and washed with 1.25 liter of double-distilled water and then 125 ml of 50 mM sodium phosphate, pH 7.2. After washing, the beads were returned to the original flask, which was rinsed prior to the beads being replaced, and then 125 ml of 4 mM ADH, 50 mM sodium phosphate (pH 7.2). The pH of the buffer was then checked to ensure that the pH was about neutral, and then the flask was returned to the shaker for low speed agitation for 2 hours.

While the beads were shaking, the primary antibody solution was prepared. The primary antibody (0-2 mg), 5 mg of $NaIO_4$, and enough PBS to raise the volume to 1.0 ml were combined in a 1.5 ml plastic tube (Eppendorf). The contents were mixed by vortexing until all the ingredients had dissolved. Next, a 10-ml desalting column was prepared by washing with 50 ml of PBS (pH 7.2). The washed column was then loaded with the 1.0 ml solution of primary antibody, followed by elution with 8 ml of PBS (pH 7.2). The eluate was collected in a reclosable 15-ml plastic tube, and the presence of the antibody in the eluate was confirmed by checking the absorbance at 280 nm.

The flask containing the beads was then removed from the shaker, and 125 mg of $NaBH_4$ was added to the flask. The flask was then returned to the shaker for 30 minutes at low speed. The beads were then removed from the flask and washed successively with 1.25 liter of double-distilled water, 250 ml of 50 mM sodium phosphate (pH 7.2) containing 1 M NaCl, and 250 ml PBS (pH 7.2). The washed beads were then placed in a fresh 1-liter flask, to which was added 113 ml of PBS (pH 7.2) and the primary antibody solution. The flask was then placed on a shaker and the contents were agitated at low speed for 1 hour. The foil-capped flask was then chilled overnight at 4° C.

The next day, 125 mg of $NaBH_4$ was added to the flask, and the flask was placed on a shaker and agitated at low speed for 30 minutes.

Following agitation, the beads were washed successively with 1.25 liter of 50 mM sodium phosphate (pH 7.2), 250 ml of 50 mM sodium phosphate (pH 7.2) containing 1 M NaCl, and 250 mL Tris-HCl (pH 7.2). After washing, the beads were poured into a flat glass tray and covered with filter-sterilized 2% BSA/0.02% $NaN_3$. The beads were then separated into aliquots in sterile plastic containers and covered with excess 2% BSA/0.02% $NaN_3$. The containers were then shaken at low speed for 1 hour with swirling every 30 minutes. The beads were then stored at 4° C. until use.

EXAMPLE 19

Materials and Methods
Chemical Reagents
Borosilicate glass beads (3 mm diameter, $7.5 \times 10^{-4}$ $m^2/g$) were obtained from VWR Scientific Products. 3-Aminopropyl-triethoxysilane (APTES), succinic anhydride, 1-ethyl-3-(3-dimethylaminopropyl) carbodiimide (EDC), morpholineethanesulfonic acid (MES) ovalbumin, (OVA), and bovine serum albumin (BSA) were obtained from Sigma Chemical Co. (St. Louis, Mo.). PEG-dicarboxymethyl (MW 3,400) was obtained from Shearwater Polymers, Inc. (Huntsville, Ala.) and the BCA protein assay kit was obtained from Pierce Chemical, Co. (Rockford, Ill.). *Bacillus globigii* (BG) spores were provided by Dugway Proving Ground (Dugway, Utah). *E.coli* 0157:H7 was purchased from ATCC, and rehydrated in Tryptic Soy Broth (TSB) at 37° C. All other reagents required in the coupling and wash buffers were analytical grade.

Antibodies
Monoclonal mouse anti-chicken egg ovalbumin (anti-OVA, clone OVA-14) and monoclonal mouse anti-BSA (anti-BSA, clone BSA-33) were purchased from Sigma Chemical Co (St. Louis, Mo.). Polyclonal goat anti-*E.coil* 0157:H7 was obtained from Kirkegaard & Perry Laboratory (Gaithersburg, Md.) Monoclonal goat anti-*Bacillus globigii* was kindly provided by Dugway Proving Grounds (Dugway, Utah).

Immobilization
Glass beads, 200 g, were cleaned in concentrated nitric acid for 1 hr in a boiling water bath. Beads were derivatized with 3-aminopropyltriethoxy silane according to M. K. Walsh & H. E. Swaisgood, Characterization of a chemically conjugated beta-galactosidase bioreactor, 17 J. Food Biochem. 283-292 (1993). Half of the beads, 100 g, were succinylated with succinic anhydride in 0.1 M sodium acetate buffer, pH 4.0, for 2 hours. Dry succinic anhydride, 10 g, was added to 150 ml of sodium acetate buffer for succinylation. The APTES and succinylated glass beads were dried overnight at 80° C. and stored at room temperature.

Dicarboxymethyl-PEG was covalently attached to APTES-modified glass beads using a one-step EDC reaction according to G. T. Hermanson et al., Immobilized Affinity Ligand Techniques 80-83 (Academic Press, New York 1992). To 100 g beads, 100 ml of 0.1 M MES, (pH 4.5) containing 10 mM dicarboxymethyl-PEG and 500 mg of EDC were added and incubated at 25° C. with shaking (150 rpm) for 2 h. The PEG-modified beads were washed with PBS, pH 7.4, and dried at 25° C. Anti-OVA IgG, anti-BG IgG and anti-*E. coli* IgG were attached to PEG and succinylated beads using the one-step EDC reaction. To 100 g of beads, 1 mg of antibody in 150 mL of 0.1 M 0.1 M MES buffer (pH 4.5) was added. EDC, 500 mg, was added and incubated at 25° C. for 2 hours. After washing antibody-modified beads (Ab-beads) 5 times with 50 ml PBST, BSA, 3% in PBST, was added and incubated overnight to block nonspecific binding sites on the glass surface.

The BCA protein assay was employed to determine the amount of protein immobilized on the glass beads according to M. Bonde et al., Direct dye binding-a quantitative assay for solid-phase immobilized protein, 200 Anal. Biochem. 195-198 (1992), prior to blocking with BSA. Antibody-modified beads, 8 g, were incubated with 5 mL of BCA reagent for 30 min at 37° C. The amount of immobilized antibody was determined based on BSA as the standard.

Detection of Captured OVA, BG Spores and *E. coli* 0157:H7

Capture of OVA, BG spores and *E. coli* 0157:H7 onto Ab-beads was detected using a surface ELISA method. To 8 g of Ab-beads, 10 mL of appropriate antigen dilution (OVA, BG, or *E. coli* 0157:H7) was added and incubated at 25° C. for 1 h on a shaker (150 rpm). Beads were then washed five times with 50 mL PBST (pH 7.2). Specific antibody (40 µg/10 mL PBST) was added to the washed beads and incubated at 25° C. for 1 h at 150 rpm. Beads were washed five times with 50 mL PBST (pH 7.2) before addition of tertiary antibody, anti-IgG-HRP, 1 µg in PBST. Beads were incubated at 25° C. for 1 h at 150 rpm followed by washing five times with 50 mL PBST (pH 7.2). The substrate for HRP (5 mL of tetramethyl benzidine) was added to the beads and incubated in the dark for 15 min. The liquid, 1 ml, was removed from the beads and the absorbance at 370 nm was measured with a Cary-100-Bio Spectrophotometer (Varian Inst., Sugarland, Tex.).

Results and Discussion
Immobilized Antibodies
The results determined by the BCA protein assay indicated that approximately the same amount of protein was immobilized onto both the succinylated and PEG-modified beads. Considering the surface area of the 3 mm glass beads ($7.5 \times 10^{-4}$ $m^2/g$), the theoretical maximum amount of immobilized antibody was 15 mg antibody/$m^2$. These results are consistent with other investigators, P. J. Soltys & M. R. Etzel, Equilibrium Absorption of LDL and gold Immunoconjugates to Affinity Membranes Containing PEG Spacers, 21 Biomaterials 37-48 (2000), for a monolayer of immobilized antibody.

Figure 17A:
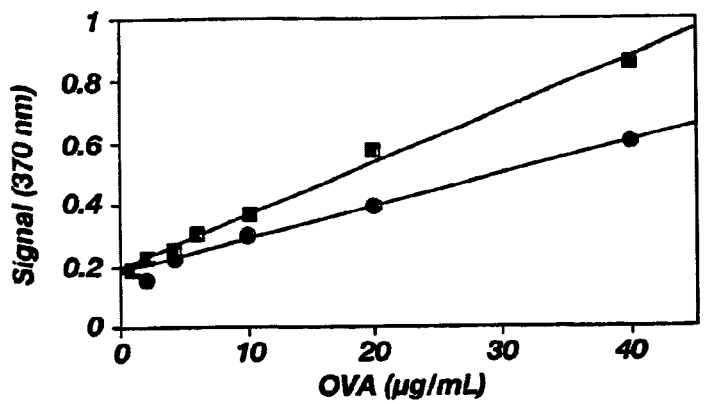
FIGS. 17A-C show calibration plots of the relative capture activity versus concentration of antigen. Two types of glass beads, succinylated (●) and PEG-coupled (■), were used.
Figure 17B:
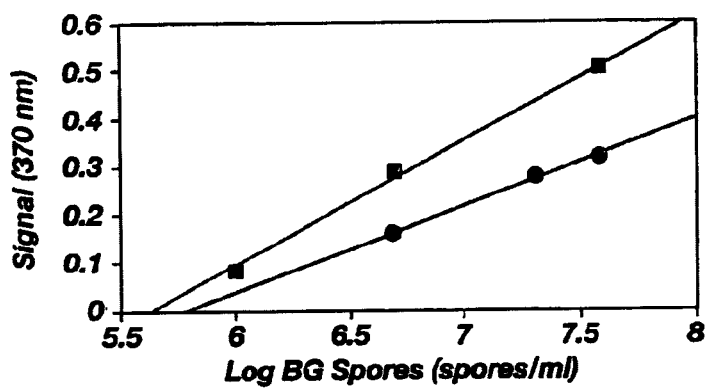
Figure 17C:
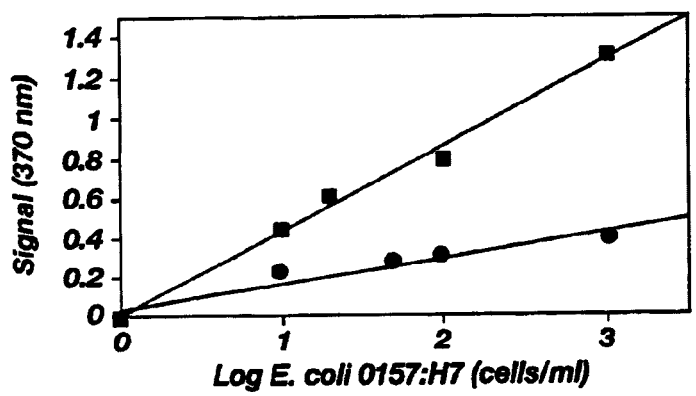

Comparison of Relative Capture Efficiency
The calibration plots for capturing OVA, BG spores and *E.coli* 0157:H7 cells are shown in FIGS. 17A, B, and C. Signal at 370 nm indicates the amount of tertiary antibody, anti-IgG-HRP, bound to the surface. Succinylated Ab-beads captured OVA, BG spores and *E. coli* 0157:H7, but the capture efficiency was less than the PEG Ab-beads. The slope of the PEG Ab-beads are higher compared to the succinylated Ab-beads for each antigen tested. The influence of a PEG spacer is more dramatic in the capture of *E. coli* O157:H7.

The observed difference in capture efficiency of PEG versus succinylated Ab-beads can be explained by the long arm PEG provides which distances the antibodies from the support surface. This allows greater accessibility of the antigens to the immobilized antibodies, reducing the amount of steric hindrance. Since the total amount of antibodies immobilized onto succinylated and PEG beads was similar, the antibodies immobilized via a spacer may have been able to capture the antigen more effectively.

EXAMPLE 20

Surface Modification. The capture ability of antibodies attached to different spacers was investigated (see Table 4). Dextran (MW 37,500; Sigma, St. Louis, Mo.), polyethylene glycol-dicarboxylmethyl (PEG, MW 3,400; Shearwater Polymers, Inc., Huntsville, Ala.), or polythreonine (MW 12,100; Sigma, St. Louis, Mo.) were used as spacers.

Anti-BSA Ab were bound to 2.8 µm tosyl-activated polystyrene Dynalbeads (1 mg). Polythreonine (MW 12,100; Sigma) was used as spacer and attached to the beads by the method of M. Blake & B. C. Weimer, Immunomagnetic detection of *Bacillus stearothermophilus* spores in food and environmental samples, 63 Appl. Environ. Microbiol. 1643-1646 (1997). A total of 100 µl ($10^8$ total beads) modified polystyrene beads were used for each sample. Anti-OVA Ab at a concentration of $10^{16}$ molecules/m² were bound to 3 mm glass beads by the method as described above. PEG was used as spacer and attached using the EDC facilitated reaction. G. T. Hermanson, supra. Anti-*B. globigii* spore Ab were bound to 3 mm glass and 7 mm ceramic beads. Polythreonine was used as the spacer for the ceramic beads, whereas PEG and dextran were used as spacers with glass beads. G. T. Hermanson, supra. The antibody concentration was $10^{16}$ molecules/m² for all anti-*B. globigii* spore beads. Anti-*E. coli* O157:H7 (Kirkegaard & Perry Laboratory, Gaithersburg, Md.) was attached to 3 mm glass beads using PEG as the spacer (as described above) at a concentration of $10^{13}$ molecules/m². Hybridization slides (2.4 cm² surface area) were also modified with the same concentration of anti-*E. coli* O157:H7 antibodies using PEG as the spacer.

Detection in Static Environment. Eight grams of Ab modified beads were placed into a 50 ml centrifuge tube and 10 ml of sample was added to the beads. Samples were incubated on a rocker for 1 h at 25° C. The samples were washed six times each with 50 ml PBST (pH 5.8). Secondary Ab was added (total of $10^{12}$ molecules of anti-*E. coli* O157:H7, $10^{13}$ molecules of anti-OVA, $10^{13}$ molecules of anti-BSA, and $10^{12}$ of anti-*Bacillus globigii*) in 10 ml PBST and beads were again incubated for 1 h. Samples were washed six times with 50 ml PBST (pH 5.8) and incubated with 10 ml of anti-IgG conjugated to horseradish peroxidase (Pierce Chemical Company, Rockford, Ill.; IgG-HRP, 1 µg/10 ml PBST, pH 5.8). After the last wash step, beads were added to 5 ml of 1-Step Turbo TMB-ELISA substrate (Pierce) and incubated in the dark for 20 min before a reading was taken at $A_{370}$ using a Cary 100-Bio UV/Visible spectrophotometer (Varian, Sugar Land, Tex.). Water blanks were used to zero the instrument.

Detection using Flow. Flow used a fluidized bed of beads, 8 g for the small unit and 250 g for the large unit, with Ab covalently bound. To generate flow, a vacuum pump was used. The reagents were evacuated from the bead cartridge through the top of the reactor at a constant rate of 0.4 L/min (or 5" of Hg). As soon as all the liquid passed over the beads the next reagent was allowed to flow through the reactor. This continued until all the reagents flowed across the beads. Just before adding the substrate (TMB) to the bead cartridge, the vacuum was turned off and the TMB was pulled into the reactor with a syringe. Once the TMB solution covered the beads, the cartridge was sealed and placed in the dark for 20 min. To measure the color development at $A_{370}$, 1 ml of the substrate was placed in a cuvette. Water blanks were used to zero the spectrophotometer.

Four liters of 0.25 M sodium phosphate buffer (pH 7.0) or river water were spiked with $10^6$ total *Bacillus globigii* spores. A stainless steel module was filled with 250 g modified anti-*B. globigii* spore ceramic beads. The *B. globigii* spore solution was recycled over the 7 mm modified ceramic beads for 60 min at 1, 2, and 4 L/min flow rates. Five beads were taken out every 15 min, replaced by 5 non-modified ceramic beads, and capture ability of the beads investigated using the static method. At the same time spore counts were determined on plate count agar.

The ability of the detection system to recover *B. globigii* spores from various environmental and industrial water samples was also investigated. Samples were collected from various environmental and industrial locations in Cache Valley, Utah: (A) Logan River water (pH 8.4); (B) Gossner's Cheese Plant tank water (pH 9.2); (C) PBST (pH 7.2); and (D) Utah State University Dairy Plant slush tank (pH 7.2). Samples were tested in flow using 8 g of Ab modified beads. Standard curves were generated in these samples with pure cultures in buffer. The ability of the detection system to recover *E. coli* O157:H7 from meat extract and PBST samples was also investigated with $10^4$ total cells and anti-*E. coli* O157:H7 Ab attached to 3 mm glass beads via PEG.

TABLE 4

List of antibodies and their modifications used to capture bovine serum albumin (BSA), egg albumin (OVA), *B. globigii* spores, and *E. coli* O157:H7.

| Antibody | Bead | Size | Spacer | Matrices tested |
|---|---|---|---|---|
| Anti-BSA | polystyrene | 2.8 µm | polythreonine | PBS |
| Anti-OVA | Glass | 3 mm | PEG | PBS |
| Anti-*B. globigii* spores | Glass | 3 mm | PEG and dextran | Environmental and industrial water samples, 0.25 M sodium phosphate buffer, pH 7.2 |
| | Ceramic | 7 mm | polythreonine | |
| Anti-*E. coli* O157:H7 | Glass | 3 mm | PEG | PBS, meat |

RESULTS

Figure 18:
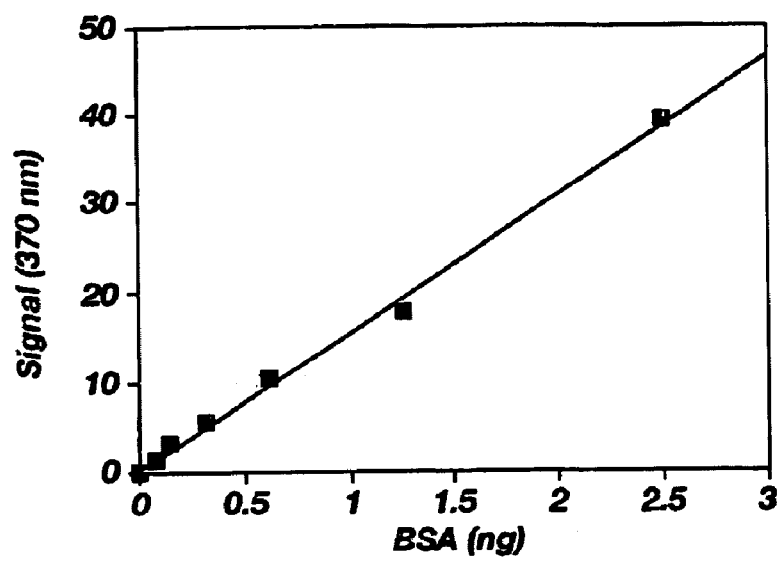
FIG. 18 shows a standard curve for BSA capture with tosyl-activated, polythreonine-modified immunomagnetic beads. Standard error of the mean at each data point is masked by the symbol.

Static capture ability of modified beads. FIG. 18 shows the standard curve obtained with anti-BSA-modified immunomagnetic beads and static detection. Ab modified polystyrene beads, $10^8$ total beads, successfully captured BSA. Very small amounts (<1 ng) of BSA can be detected with these beads. The linear response of signal to BSA increase was 99.7%, which makes this test very sensitive.

Figure 19:
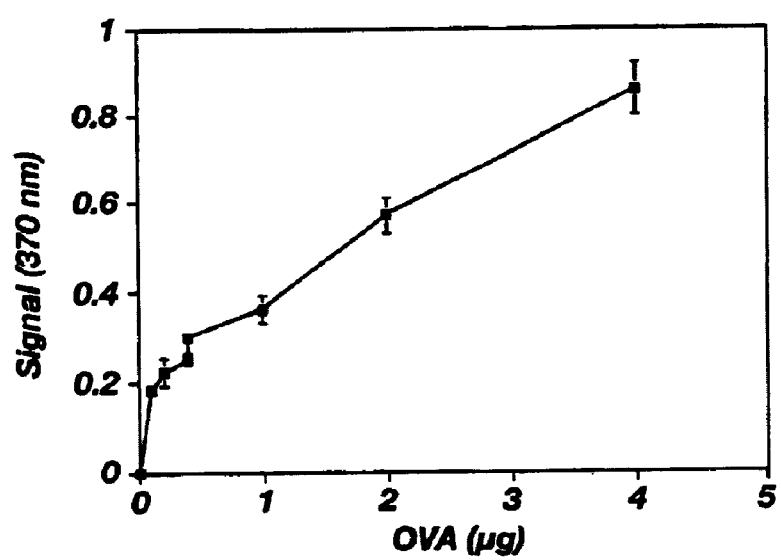
FIG. 19 shows a standard curve of OVA using 3 mm PEG-modified glass beads. Error bars represent standard error of the mean.

FIG. 19 shows the standard curve obtained for 3 mm PEG-anti-OVA-modified beads tested in static. The lower limit of detection is 0.2 µg. There is a linear response of signal increase to OVA increase between 0.2 to 4.0 µg. We did not test beyond 4 µg, because our objective was to develop a test that was sensitive on the lower end.

Flow Capture Ability of Modified Beads.

Figure 20A:
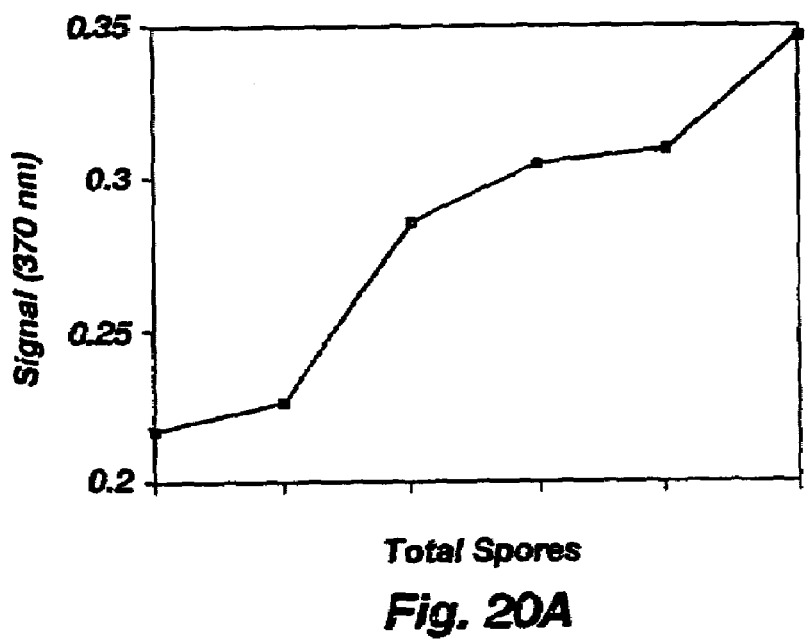
FIGS. 20A&B show standard curves of *B. globigii* spores in PBST (FIG. 20A) and *E. coli* O157:H7 in meat extract (□) and PBST (■) (FIG. 20B) using 3 mm PEG-modified glass beads. Standard error of the mean for each data point is masked by the symbol.
Figure 20B:
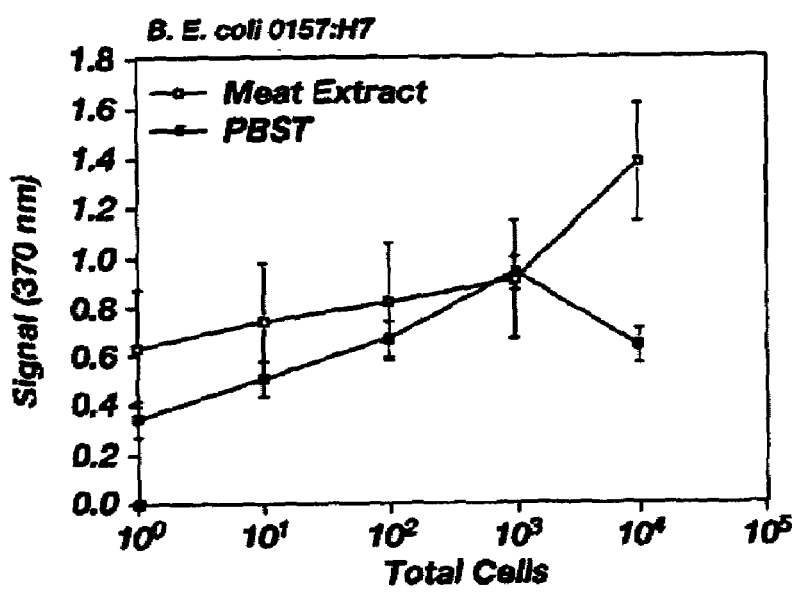

FIG. 20A shows the standard curves obtained for *B. globigii* spore capture at a constant sample flow of 0.4 m L/min using 8 g of 3 mm PEG modified glass beads. A linear increase in signal was observed as spore concentration increased. FIG. 20B shows the Immuno capture of *E. coli* O157:H7 at a constant sample flow rate of 0.4 L/min with 8 g of 3 mm PEG modified glass beads. To observe the influence of sample composition, PBST and sterile meat extract were used. Meat extract spiked with cells consistently showed a higher signal as compared to cells spiked into buffer.

Figure 21:
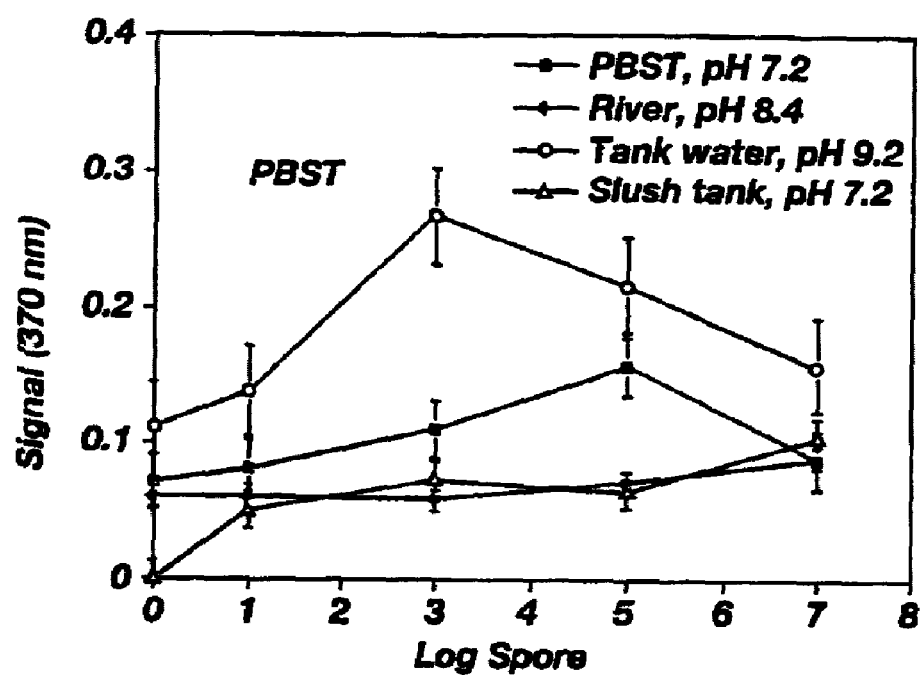
FIG. 21 shows standard curves of *B. globigii* spores in environmental and industrial water samples using PEG-modified glass beads: PBST (■), river water (♦), tank water (○), slush tank (Δ). Error bars represent standard error of the mean.

FIG. 21 shows the standard curve obtained for *B. globigii* spores spiked into the various environmental and industrial water samples. All samples were sterilized prior to the addition of *B. globigii* spores. No linear response to increased spore concentration was observed using river or slush tank water. This results in a constant flat line as seen in FIG. 21. A linear response was observed using tank water from Gossner's Cheese Plant and PBST. The lower limit of detection for both tank water and PBST was 1 spore/sample. However, the upper limit with PBST was $10^5$ total spores and for tank water $10^3$ total spores. All environmental and industrial samples had pHs values ranging from 7.2 to 9.2. The beads were active and captured spores over this range.

The invention claimed is:

1. A method for capturing and concentrating a selected antigen from an aqueous medium containing a mixture of antigens comprising:

(a) causing a first volume of the aqueous medium containing the mixture of antigens to flow through a module containing at least two antibody-bead conjugates, wherein each of the antibody-bead conjugates comprises a bead, a polymeric spacer comprises polythreonine covalently coupled to the bead, and an antibody covalently coupled to the polymeric spacer, wherein the antibody is configured for binding the selected antigen, at a first flow rate such that the antibody-bead conjugates form a fluidized bed and the selected antigen binds to the antibody-bead conjugates;

(b) washing the antibody-bead conjugates having the selected antigen bound thereto by causing a wash medium to flow through the module at a second flow rate such that the antibody-bead conjugates having the selected antigen bound thereto form a fluidized bed; and (c) holding the washed antibody-bead conjugates having the selected antigen bound thereto in a second volume of a second wash medium, wherein the second volume is smaller than the first volume.

2. The method of claim 1 wherein the aqueous medium containing the mixture of antigens comprises a food.

3. The method of claim 1 wherein the aqueous medium containing the mixture of antigens comprises an environmental sample.

4. The method of claim 1 wherein the bead is a glass bead.

5. The method of claim 1 wherein the bead is a ceramic bead.

6. A method for capturing and concentrating a selected antigen from an aqueous medium containing a mixture of antigens comprising:

(a) causing a first volume of the aqueous medium containing the mixture of antigens to flow through a module containing at least two antibody-bead conjugates, wherein each of the antibody-bead conjugates comprises a bead having a diameter of about 1 to 7 millimeters, a polymeric spacer covalently coupled to the bead, and an antibody covalently coupled to the polymeric spacer, wherein the antibody is configured for binding the selected antigen, at a first flow rate such that the antibody-bead conjugates form a fluidized bed and the selected antigen binds to the antibody-bead conjugates;

(b) washing the antibody-bead conjugates having the selected antigen bound thereto by causing a wash medium to flow through the module at a second flow rate such that the antibody-bead conjugates having the selected antigen bound thereto form a fluidized bed; and (c) holding the washed antibody-bead conjugates having the selected antigen bound thereto in a second volume of a second wash medium, wherein the second volume is smaller than the first volume.

7. The method of claim 1 wherein the antibody comprises a monoclonal antibody.

8. The method of claim 1 wherein the antibody comprises a polyclonal antibody.

9. The method of claim 1 wherein the antibody comprises an antibody fragment.

10. The method of claim 1 wherein flow is caused by pumping.

11. The method of claim 1 wherein flow is caused by applying partial vacuum.

12. The method of claim 1 wherein said first flow rate is about 0.2 to 1.2 liters/minute.

13. The method of claim 12 wherein the first flow rate is about 0.3 to 0.7 liters per minute.

14. A method for capturing and concentrating a selected antigen from an aqueous medium containing a mixture of antigens comprising:

(a) causing a first volume of the aqueous medium containing the mixture of antigens to flow through a module containing at least two antibody-bead conjugates, wherein each of the antibody-bead conjugates comprises a 1-7 millimeter glass or ceramic bead, a dextran or polyethylene glycol spacer covalently coupled to the bead, and an antibody covalently coupled to the spacer, wherein the antibody is configured for binding the selected antigen, at a first flow rate such that the antibody-bead conjugates form a fluidized bed and the selected antigen binds to the antibody-bead conjugates;

(b) washing the antibody-bead conjugates having the selected antigen bound thereto by causing a wash medium to flow through the module at a second flow rate such that the antibody-bead conjugates having the selected antigen bound thereto form a fluidized bed; and (c) holding the washed antibody-bead conjugates having the selected antigen bound thereto in a second volume of a second wash medium, wherein the second volume is smaller than the first volume.

15. The method of claim 14 wherein the aqueous medium containing the mixture of antigens comprises a food.

16. The method of claim 14 wherein the aqueous medium containing the mixture of antigens comprises an environmental sample.

17. The method of claim 14 wherein the polymeric spacer comprises a polyamino acid.

18. The method of claim 17 wherein the polyamino acid comprises polythreonine.

19. The method of claim 17 wherein the polyamino acid comprises polyserine.

20. The method of claim 14 wherein the antibody comprises a monoclonal antibody.

21. The method of claim 14 wherein the antibody comprises a polyclonal antibody.

22. The method of claim 14 wherein the antibody comprises an antibody fragment.

23. The method of claim 14 wherein flow is caused by pumping.

24. The method of claim 14 wherein flow is caused by applying partial vacuum.

25. The method of claim 14 wherein said first flow rate is about 0.2 to 1.2 liters/minute.

26. The method of claim 25 wherein the first flow rate is about 0.3 to 0.7 liters per minute.

* * * * *